United States Patent
Fukunaga et al.

(10) Patent No.: US 6,740,242 B2
(45) Date of Patent: May 25, 2004

(54) PLATING APPARATUS AND METHOD OF MANAGING PLATING LIQUID COMPOSITION

(75) Inventors: Akira Fukunaga, Tokyo (JP); Hiroshi Nagasawa, Tokyo (JP)

(73) Assignee: Ebara Corporation, Tokyo (JP)

( * ) Notice: Subject to any disclaimer, the term of this patent is extended or adjusted under 35 U.S.C. 154(b) by 0 days.

(21) Appl. No.: 09/994,755

(22) Filed: Nov. 28, 2001

(65) Prior Publication Data

US 2002/0063097 A1 May 30, 2002

(30) Foreign Application Priority Data

Nov. 29, 2000 (JP) ........................................ 2000-362559

(51) Int. Cl.$^7$ .............................................. B01D 15/08
(52) U.S. Cl. .................... 210/656; 210/198.2; 210/659; 427/8; 436/161; 702/23
(58) Field of Search ................................ 210/656, 654, 210/198.2; 118/688; 422/62, 70; 427/8; 702/23; 436/161

(56) References Cited

U.S. PATENT DOCUMENTS

| | | | | |
|---|---|---|---|---|
| 3,920,397 A | * | 11/1975 | Small | 23/230 R |
| 4,326,940 A | * | 4/1982 | Eckles et al. | 204/232 |
| 4,554,254 A | * | 11/1985 | Krystal | 436/86 |
| 4,788,700 A | * | 11/1988 | Kurozumi et al. | 378/44 |
| 4,800,132 A | * | 1/1989 | Grunwald et al. | 428/560 |
| 4,950,504 A | * | 8/1990 | Grunwald et al. | 427/242 |
| 5,196,096 A | * | 3/1993 | Chang et al. | 204/153.1 |
| 5,279,972 A | * | 1/1994 | Heckenberg et al. | 436/178 |
| 5,296,124 A | * | 3/1994 | Eliash et al. | 204/402 |
| 5,338,448 A | * | 8/1994 | Gjerde | 270/198.2 |
| 5,670,054 A | * | 9/1997 | Kibbey et al. | 210/656 |
| 5,772,889 A | * | 6/1998 | Gjerde et al. | 210/635 |
| 6,017,427 A | * | 1/2000 | Yamamoto | 204/212 |
| 6,151,113 A | * | 11/2000 | O'Donohue | 356/338 |
| 6,210,571 B1 | * | 4/2001 | Zambias et al. | 210/198.2 |
| 6,229,605 B1 | * | 5/2001 | Benedict | 356/339 |
| 6,362,880 B1 | * | 3/2002 | Anderson | 356/337 |
| 6,379,520 B1 | * | 4/2002 | Kuriyama et al. | 205/81 |
| 6,521,358 B1 | * | 2/2003 | Tanaka et al. | 428/670 |

OTHER PUBLICATIONS

Heberling, "Monitoring Acid Copper Plating Baths" PC FAB Aug. 1989 pp. 72–84.*

* cited by examiner

Primary Examiner—Ernest S. Therkorn
(74) Attorney, Agent, or Firm—Wenderoth, Lind & Ponack, L.L.P.

(57) ABSTRACT

A plating apparatus comprises a plating unit having a plating bath for holding a plating liquid therein, and a planting monitoring unit having a liquid chromatography device and an arithmetical unit. The liquid chromatography device serves to separate and quantify an additive in a sample of the planting liquid. The arithmetical unit serves to compare a quantified value of the additive with a given concentration predetermined for the additive and to produce an output signal representing the compare result. The plating apparatus further comprises an additive replenishing unit for adding a solution including the additive from an additive tank to the plating liquid in the planting bath based on the output signal from the arithmetical unit in the plating liquid monitoring unit.

4 Claims, 22 Drawing Sheets

PLATING APPARATUS AND METHOD OF MANAGING PLATING LIQUID COMPOSITION

BACKGROUND OF THE INVENTION

1. Field of the Invention

The present invention relates to a plating apparatus and a method of managing a plating liquid composition. More particularly, the invention relates to a plating apparatus for forming an interconnection by embedding copper in a fine interconnection groove defined in a surface of a semiconductor substrate through copper sulfate plating, and a method of managing an additive in a plating liquid used in such a plating apparatus.

2. Description of the Related Art

Processes of depositing a metal film by plating have widely been used in electronic industries for manufacturing a printed circuit board and the like. Recently, there have been made more attempts to use copper (Cu) as a metal material for forming interconnection circuits on semiconductor substrates because of its low electric resistivity and high resistance to electromigration, instead of aluminum or aluminum alloy. Copper interconnections are generally formed by embedding copper in fine recesses defined in a surface of a semiconductor substrate. Processes for forming copper interconnections include a chemical vapor deposition (CVD) process, a sputtering process, and a plating process. In any of these processes, a copper film is deposited on the entire surface of the semiconductor substrate, and then unwanted deposited copper is removed from the semiconductor substrate by chemical mechanical polishing (CMP).

FIGS. 1A through 1C show an example of a process for forming a copper interconnection on a substrate W through copper plating. As shown in FIG. 1A, an oxide film 2 of SiO2 is deposited on an electrically conductive layer 1a on a semiconductor base 1 on which a semiconductor device has been formed. A contact hole 3 and an interconnection groove 4 are formed in the oxide film 2 by a lithography etching technology. Then, a barrier layer 5 made of TaN or the like is formed on the oxide film 2, and a seed layer 7, which is used as a feeding layer in an electrolytic plating, is formed on the barrier layer 5.

Subsequently, as shown in FIG. 1B, the surface of the substrate W is plated with copper to fill the contact hole 3 and the interconnection groove 4 with copper and to form a copper film 6 on the oxide film 2. Thereafter, the surface of the substrate W is polished to remove the copper film 6 from the oxide film 2 so that the surface of the copper film 6 filled in the contact hole 3 and the interconnection groove 4 is made substantially even with the surface of the oxide film 2. Thus, as shown in FIG. 1C, an interconnection comprising the copper film 6 is formed.

The seed layer 7 is generally formed by sputtering or CVD. The copper film 6 is formed by an electrolytic copper plating process using a plating liquid which generally comprises a copper sulfate plating liquid including copper sulfate and sulfuric acid.

As circuit interconnections become finer, interconnection grooves or plugs have higher aspect ratios. In view of such tendencies, a strict technical requirement has been imposed for completely embedding copper in fine recesses, 0.1 μm or less wide, defined in substrates, without causing defects.

To meet such a requirement, it is necessary to optimize a geometrical shape of an electrolytic tank and operating conditions such as electric conditions in the plating process. However, it is most important to completely manage the composition of the plating liquid. The plating liquid comprises main components including metal ions to be deposited and counter ions thereof, and additives for locally controlling the rate of the deposition reaction to equalize the deposition of the metal ions on a surface to be plated. Although the amount of additives added is extremely small, the additives have a highly significant effect on the plating process. Therefore, the plating process may disadvantageously be affected by the additives unless the additives are strictly managed in their concentrations.

In recent years, it has been required to minimize loads on the environment in various production processes. Particularly, it is expected to use a plating bath for a longer time in the plating process, which is highly likely to produce a waste liquid having a high concentration. From these points of view, it is desirable to positively manage the concentration of the plating liquid for efficiently using the plating liquid.

Heretofore, however, almost no efforts have been made to manage plating liquids. In a conventional plating process, certain amounts of plating liquid components are added to the plating liquid at given intervals of time for replenishment, and a plating bath is replaced as a whole after the plating liquid components have been added a certain number of times.

In an electric plating process, the state of the deposition reaction is monitored based on electrochemical measurement such as cyclic voltammetric stripping (CVS), and information on the concentrations of additives is obtained indirectly from the measured results. In this CVS process, a cyclic voltammogram is plotted with use of a potentiostat and a potential scanner, and information on the concentrations of the additives and contaminants in the plating liquid is obtained indirectly from the shape of the plotted cyclic voltammogram. However, since the CVS process is based on an indirect approach, it cannot meet requirements for management of the plating liquid with higher accuracy.

SUMMARY OF THE INVENTION

The present invention has been made in view of the above drawbacks. It is therefore an object of the present invention to provide a plating apparatus which directly separates and quantifies an additive in a plating liquid to manage a composition of the plating liquid with high accuracy, and a method of managing a composition of a plating liquid in such a plating apparatus.

According to a first aspect of the present invention, there is provided a plating apparatus comprising a plating unit having a plating bath for holding a plating liquid therein; a plating liquid monitoring unit having a liquid chromatography device for separating and quantifying an additive in a sample of the plating liquid, and having an arithmetical unit for comparing a quantified value of the additive with a given concentration predetermined for the additive and for producing an output signal representing the compared result; and an additive replenishing unit for adding a solution including the additive from an additive tank to the plating liquid in the plating bath based on the output signal from the arithmetical unit in the plating liquid monitoring unit.

With the above arrangement, the additive in the plating liquid is directly separated and analyzed (quantified) with the liquid chromatography device, and additive which is insufficient or expected to be insufficient is properly added to the plating liquid. Thus, variations in the amount of the additive in the plating liquid are kept within a certain range.

According to a preferred aspect of the present invention, the liquid chromatography device comprises an evaporative light-scattering detector for quantifying the additive. The evaporative light-scattering detector can detect the intensity of light scattered by the solute that remains unevaporated after the sample has been evaporated through spraying. Thus, the evaporative light-scattering detector can basically detect any substances and has sufficient detecting sensitivity at practical concentration levels of additives. Therefore, the evaporative light-scattering detector can simplify the entire system. In the case where the evaporative light-scattering detector has insufficient detection sensitivity for some reasons, the additives may be concentrated to a detectable level by way of pre-column concentration.

According to another preferred aspect of the present invention, the plating liquid comprises a sulfuric acid copper plating liquid for embedding copper in a fine recess defined in a substrate to form an interconnection. Ionic components are removed from the plating liquid before the additive is quantified. With this arrangement, the main components such as sulfuric acid ions, copper ions, and chlorine ions, which are present at extraordinarily high concentrations, are removed in advance. Accordingly, a trace amount of additive in the plating liquid can easily be detected.

According to still another preferred aspect of the present invention, the additive comprises at least one of an oxygen-containing water-soluble polymeric compound, a sulfur-containing organic compound, and a nitrogen-containing organic compound. The oxygen-containing water-soluble polymeric compound may comprise polyethylene glycol, polypropylene glycol, or the like. The sulfur-containing organic compound may comprise disulfide or the like. The nitrogen-containing organic compound may comprise polyamine or the like.

According to a second aspect of the present invention, there is provided a method of managing a plating liquid composition, comprising: sampling a plating liquid in a plating bath; separating and quantifying an additive in the sampled plating liquid with liquid chromatography; comparing a quantified value of the additive with a given concentration predetermined for the additive; and adding a solution including the additive to the plating liquid based on the compared result.

According to a preferred aspect of the present invention, ionic components are removed from the plating liquid in advance before the additive is quantified.

The above and other objects, features, and advantages of the present invention will become apparent from the following description when taken in conjunction with the accompanying drawings which illustrate preferred embodiments of the present invention by way of example.

DETAILED DESCRIPTION OF THE INVENTION

A plating apparatus according to embodiments of the present invention will be described below with reference to the accompanying drawings.

Figure 1A:
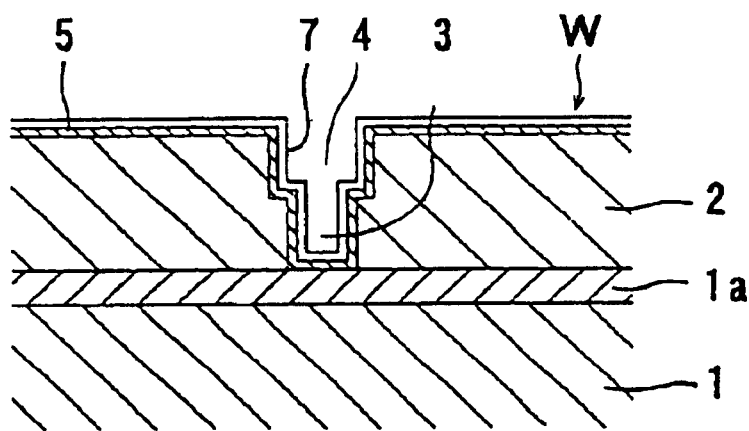
FIGS. 1A through 1C are cross-sectional views showing an example of a process for forming a copper interconnection through copper plating.
Figure 1B:
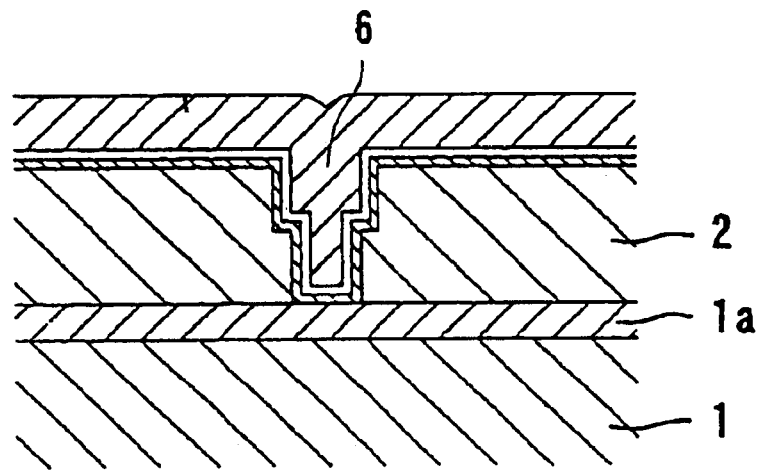
Figure 1C:
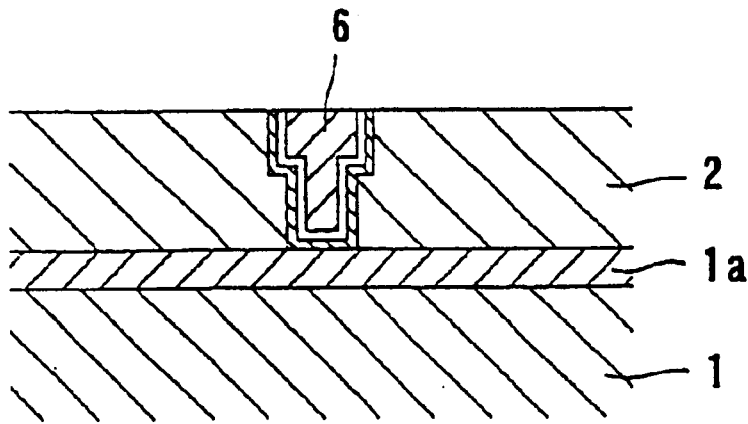
Figure 2:
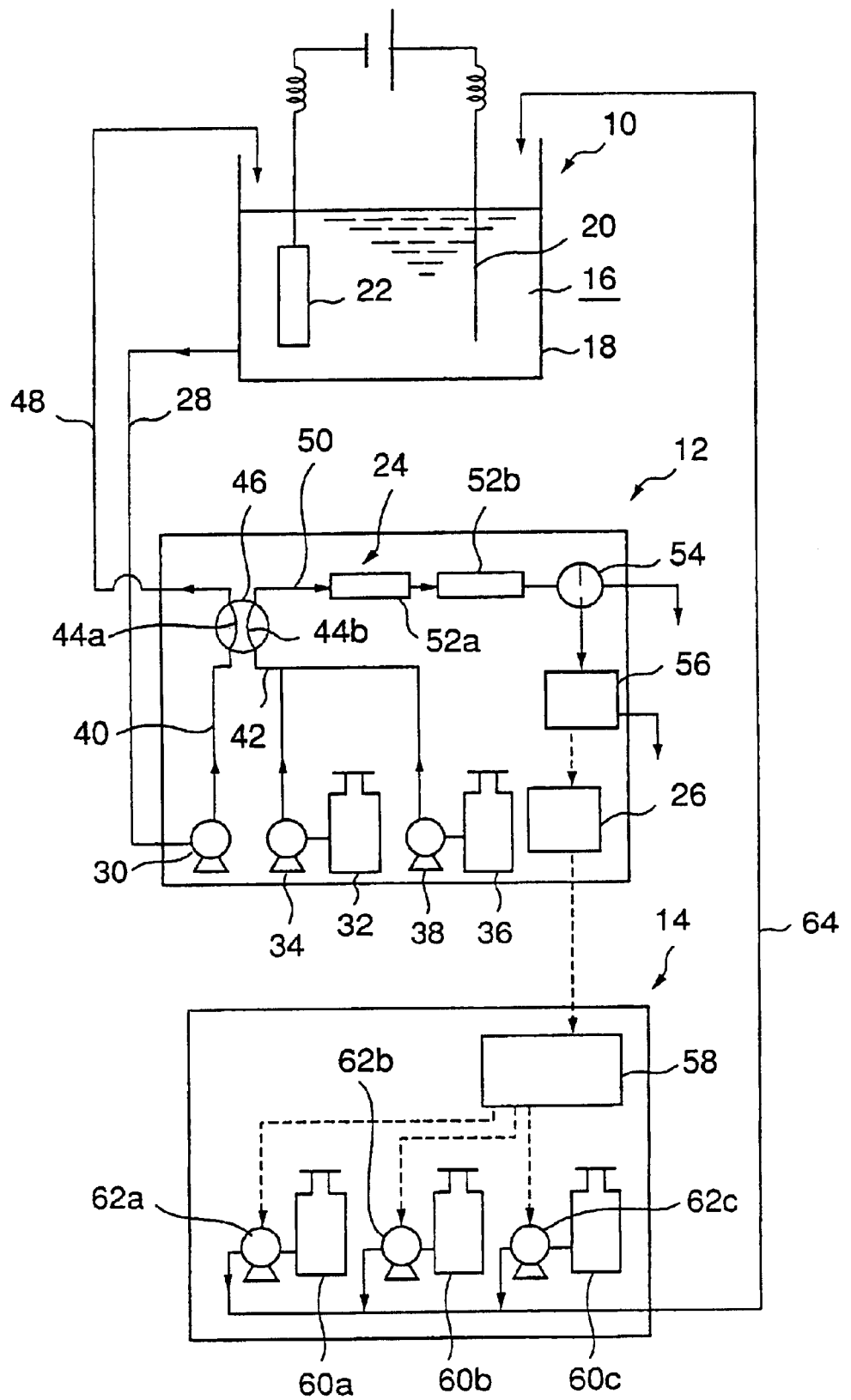
FIG. 2 is a schematic diagram showing a plating apparatus according to an embodiment of the present invention.

FIG. 2 is a schematic diagram showing a plating apparatus according to an embodiment of the present invention. The plating apparatus will be described below as an apparatus for performing an electrolytic plating process. However, the plating apparatus may basically be applicable to other plating processes.

As shown in FIG. 2, the plating apparatus mainly comprises three units, i.e., a plating unit 10, a plating liquid monitoring unit 12, and an additive replenishing unit 14. The plating apparatus also includes a power supply unit and various other units (not shown) for various purposes, in addition to the units 10, 12, 14.

The plating unit 10 comprises a plating bath 18 for holding a plating liquid 16 depending on a plating process to be carried out. The plating bath 18 houses therein an anode 20 and a workpiece 22 to be plated, and the anode 20 and the workpiece 22 are immersed in the plating liquid 16 in such a state that they are opposed to each other. The anode 20 may be soluble or insoluble in the plating liquid 16. The workpiece 22 is plated when an electric current flows between the anode 20 and the workpiece 22. The electric current may flow as a direct current or a pulsed current.

The plating liquid monitoring unit 12 comprises a liquid chromatography device 24 and an arithmetical unit 26. The liquid chromatography device 24 has a sampling pump 30 for sampling the plating liquid 16 flowing through a sample liquid introduction pipe 28 extending from the plating bath 18, a hardly soluble liquid pump 34 for delivering a hardly soluble liquid from a hardly soluble liquid tank 32, and a pure water pump 38 for delivering pure water from a pure water tank 36. The hardly soluble liquid may be selected from an organic solvent such as alcohol and a mixture of water and an organic solvent, depending on a component to be separated and the characteristics of separating columns 52a, 52b. The plating liquid monitoring unit 12 may comprise either one of the pure water supply system and the hardly soluble liquid supply system, or may have a plurality of hardly soluble liquid supply systems.

A pipe 40 extending from the sampling pump 30 and a pipe 42 extending respectively from the hardly soluble liquid pump 34 and the pure water pump 38 are connected to an injection valve 46 having two passages 44a, 44b therein. A sample liquid return pipe 48 and an analyzing system pipe 50 are connected to the injection valve 46.

When the sampling pump 30 is actuated, the plating liquid 16 in the plating bath 18 flows successively through the sample liquid introduction pipe 28, the pipe 40, the injection valve 46, and the sample liquid return pipe 48 back into the plating bath 18. When the injection valve 46 is turned 180 degrees, the passages 44a, 44b in the injection valve 46 are switched around for sampling the plating liquid in the passage 44a. When the hardly soluble liquid pump 34 and/or the pure water pump 38 is actuated, the plating liquid in the passage 44a is pushed into the analyzing system pipe 50 by the hardly soluble liquid and/or the pure water.

Two separating columns 52a, 52b are disposed on the analyzing system pipe 50 in series. The separating columns 52a, 52b serve to separate each of the additives from the sampled plating liquid with the use of chromatographic adsorption of a filling material. Generally, the separating columns 52a, 52b are selectively used depending on a component to be separated. In this embodiment, the separating columns 52a, 52b include a molecular weight fractionating column suitable for separating oxygen-containing water-soluble polymeric compounds such as polyethylene glycol and polypropylene glycol, and a somewhat hydrophobic column suitable for separating sulfur-containing organic compounds such as disulfide and nitrogen-containing organic compounds such as polyamine. These columns are connected in series for separating the aforementioned additives from the sampled plating liquid. The plating liquid monitoring unit 12 may have a single separating column, and also may have three or more separating columns connected in series.

A switching valve 54 is disposed at the downstream side of the separating columns 52a, 52b. The switching valve 54 serves to connect the separating columns 52a, 52b selectively to drainage and a detector 56. The detector 56 serves to analyze (quantify) each of additives separated by the separating columns 52a, 52b. For example, the detector 56 comprises an evaporative light-scattering detector for analyzing an additive based on an evaporative light-scattering detecting process of detecting the intensity of light scattered by the solute that remains unevaporated after the sample has been evaporated through spraying. Since the evaporative light-scattering detector can basically detect any substances and has sufficient detecting sensitivity at practical concentration levels of additives, the evaporative light-scattering detector is used in this embodiment. Thus, when an evaporative light-scattering detector is used as the detector 56, a simple system can be achieved.

Some processes of detecting a separated component utilize ultraviolet absorption or differential refraction depending on the properties of the component. Although each of these processes cannot detect all of the components by itself, these processes may be combined with each other to detect all of the components.

The detector 56 transmits an output signal to the arithmetical unit 26. The arithmetical unit 26 compares the quantitative values of the additives, which are detected by the detector 56, with given concentrations predetermined for the respective additives, and calculates differences or deviations of the additives from the given concentrations. An output signal from the arithmetical unit 26 is transmitted to a controller 58 of the additive replenishing unit 14.

The additive replenishing unit 14 comprises a controller 58, a plurality of additive tanks (three additive tanks 60a, 60b, 60c in this embodiment) for storing solutions including the respective additive, and additive pumps 62a, 62b, 62c for delivering the solutions of the additives from the additive tanks 60a, 60b, 60c. The operation of the additive pumps 62a, 62b, 62c are controlled by the controller 58. The solutions of the additives which are delivered from the additive tanks 60a, 60b, 60c through the respective additive pumps 62a, 62b, 62c are added to the plating liquid 16 in the plating bath 18 through an additive replenishing pipe 64.

A process of managing plating liquid components in the plating apparatus will be described below.

The sampling pump 30 may be operated continuously, or may be operated merely at desired sampling times. In the case where the sampling pump 30 is operated merely at desired sampling times, it is necessary for the plating solution to flow for a certain period of time until the plating solution to be analyzed is introduced into the analyzing system in order to replace the previous plating liquid that remains in the pipe of the analyzing system. The injection valve 46 is turned 180 degrees to switch around the passages 44a, 44b for sampling the plating liquid in the passage 44a in this embodiment.

Then, only the pure water pump 38 is actuated to introduce the sampled plating liquid and pure water into the separating columns 52a, 52b. At this time, the switching valve 54 is connected to drainage to drain the pure water. Main components having a high ionicity, such as sulfuric acid ions, copper ions, and chlorine ions, are not retained in the separating columns 52a, 52b at all, but flow out of the separating columns 52a, 52b. In a sulfuric acid copper plating process, for example, these main components such as sulfuric acid ions, copper ions, and chlorine ions are present at extraordinarily high concentrations, and should preferably be removed in advance for the purpose of detecting a trace amount of additives in the plating liquid.

After the main components have been drained, the switching valve 54 is turned back so as to connect to the detector 56. At the same time, the amount of pure water delivered from the pure water pump 38 is gradually reduced, and the hardly soluble liquid pump 34 is actuated to deliver the hardly soluble liquid in a gradually increasing amount to increase the concentration of methanol or the like, for example, gradually to 100%. The additives in the plating liquid are successively eluted from the separating columns 52a, 52b. Although the additives in the plating liquid are not necessarily eluted in a constant order, it has often been experienced that for a sulfuric-acid-containing organic compound, a nitrogen-containing organic compound, and an oxygen-containing water-soluble polymeric compound, the additives are eluted in the order named.

Then, these eluted additives are successively quantified by the detector 56, which transmits an output signal to the arithmetical unit 26. The arithmetical unit 26 compares the output signal (detected values) from the detector 56 with given concentrations predetermined for the respective additives, and calculates differences or deviations from the given concentrations predetermined for the respective additives. Based on the calculated data, the arithmetical unit 26 determines whether there is a shortage of any of the additives or not. If any of the additives is insufficient, the arithmetical unit 26 transmits a signal indicative of such a shortage to the controller 58. Alternatively, the arithmetical unit 26 may determine whether there will be a shortage of any of the additives within several minutes or not based on a plurality of inspection cycles, and may transmit a signal indicative of such a future shortage to the controller 58 if any of the additives will be insufficient within several minutes.

In response to a present shortage signal from the arithmetical unit 26, the controller 58 actuates the additive pump 62a, for example, to deliver the short additive from the additive tank 60a, thereby adding the additive to the plating liquid 16. Then, the controller 58 inactivates the additive pump 62a. In the case where the controller 58 receives a future shortage signal from the arithmetical unit 26, which indicates that any of the additives will be insufficient within several minutes, then the controller 58 actuates the additive pump in response to the received future shortage signal or actuates the additive pump before the several minutes elapse.

Thus, the additives in the plating liquid are directly separated and analyzed (quantified) with the liquid chromatography device 24, and those additives which are insufficient or expected to be insufficient are added to the plating liquid. Thus, variations in the amounts of additives in the plating liquid are kept within a certain range.

The evaporative light-scattering detector usually has detection sensitivity high enough to detect the practical concentration levels of the additives. In the case where the evaporative light-scattering detector has insufficient detection sensitivity for some reasons, the additives should be concentrated to a detectable level by way of pre-column concentration.

Figure 3A:
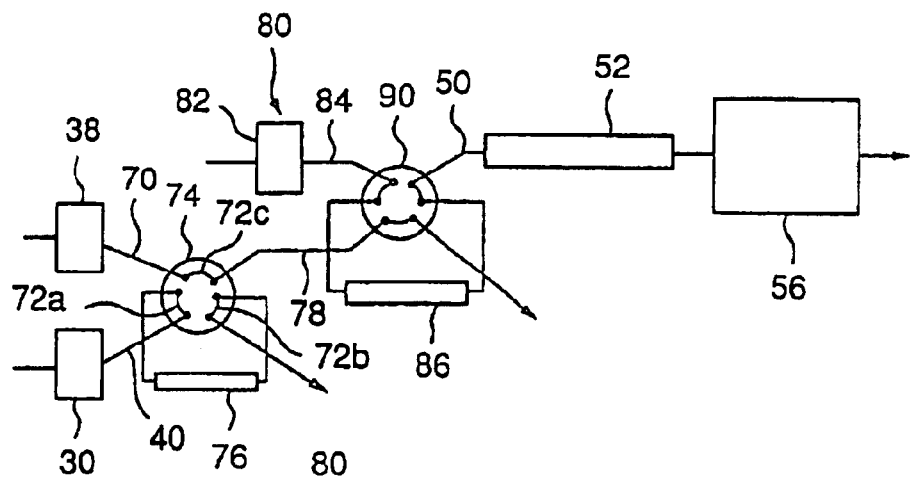
FIGS. 3A through 3C are schematic diagrams showing a system for concentrating additives of a plating liquid.
Figure 3B:
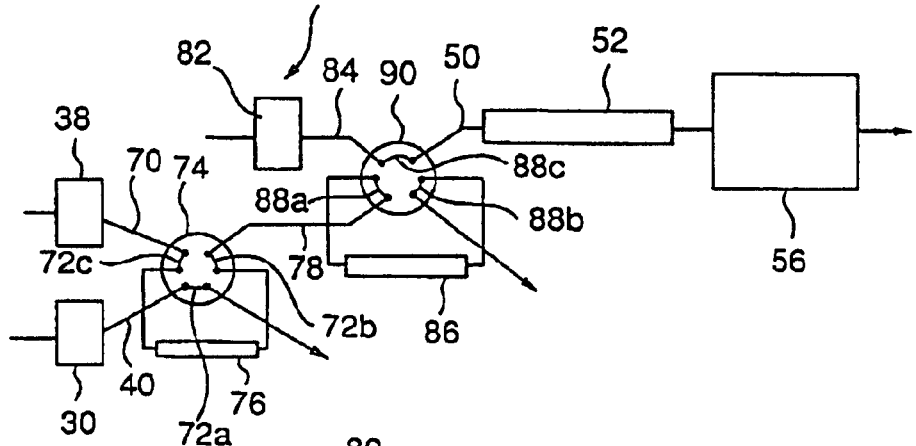
Figure 3C:
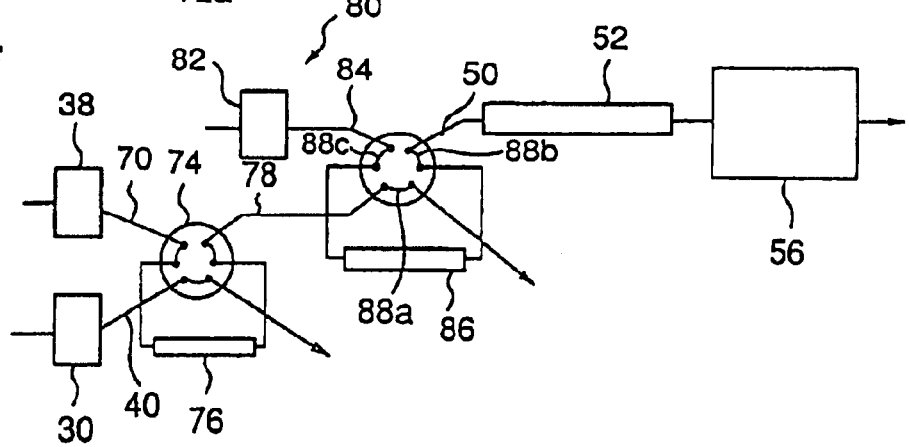

FIGS. 3A through 3C are schematic diagrams showing a system for concentrating the additives. The pipe 40 extending from the sampling pump 30 and a pipe 70 extending from the pure water pump 38 are connected to a first six-way valve 74 having three passages 72a, 72b, 72c therein. A sample extracting pipe 76 has opposite ends connected to the first six-way valve 74, and a connecting pipe 78 has an end connected to the first six-way valve 74. The other end of the connecting pipe 78, a pipe 84 extending from a pump 82 of a HPLC pump system (two-liquid gradient) 80, the opposite ends of a concentrating column 86, and the analyzing system pipe 50 are connected to a second six-way valve 90 having three passages 88a, 88b, 88c therein.

As shown in FIG. 3A, the first six-way valve 74 is arranged to connect the pipe 40 in series with the passage 72a in the first six-way valve 74, the sample extracting pipe 76, and the passage 72b in the first six-way valve 74. At this time, a sample liquid is delivered into the sample extracting pipe 76 through the sampling pump 30 for sampling. Then, as shown in FIG. 3B, the first six-way valve 74 is turned 60° counterclockwise to connect the pipe 70 in series with the passage 72c in the first six-way valve 74, the sample extracting pipe 76, the passage 72b in the first six-way valve 74, the connecting pipe 78, the passage 88a in the second six-way valve 90, the concentrating column 86, and the passage 88b in the second six-way valve 90. The sample liquid delivered into the sample extracting pipe 76 is thus introduced into the concentrating column 86 and concentrated therein. At this time, the pipe 84, the passage 88c in the second six-way valve 90, and the analyzing system pipe 50 are connected in series with each other to perform inorganic ion cleaning. Thereafter, as shown in FIG. 3C, the second six-way valve 90 is turned 60° counterclockwise to connect the pipe 84 in series with the passage 88c in the second six-way valve 90, the concentrating column 86, the passage 88b in the second six-way valve 90, and the analyzing system pipe 50. The sample liquid concentrated in the concentrating column 86 is thus introduced into the separating column 52, which separates the sample liquid into the additives. The separated additives are then analyzed (quantified) by the detector 56.

Figure 4:
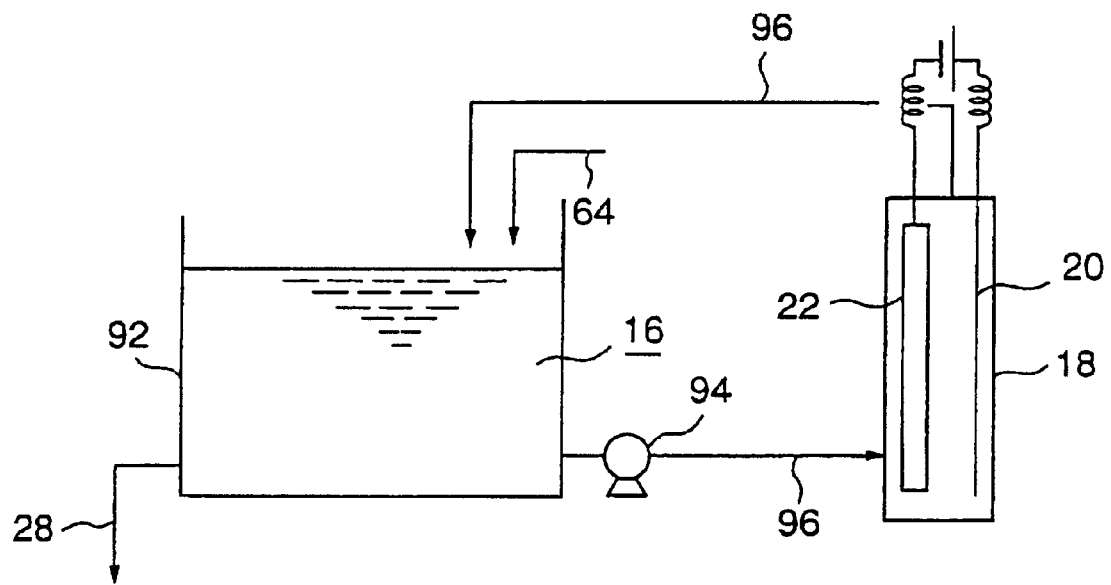
FIG. 4 is a schematic diagram of a plating apparatus according to another embodiment of the present invention.

FIG. 4 shows a plating apparatus according to another embodiment of the present invention. In this embodiment, as shown in FIG. 4, the plating apparatus has a plating liquid reservoir 92 separated from a plating bath 18. As with the embodiment shown in FIG. 2, the plating bath 18 houses therein an anode 20 and a workpiece 22 to be plated which are immersed in the plating liquid 16. The plating liquid 16 is circulated between the plating bath 18 and the plating liquid reservoir 92 through a plating liquid circulating pump 94 and plating liquid circulating pipes 96. The sample of the plating liquid 16 is introduced from the plating liquid reservoir 92 via a sample liquid introduction pipe 28 into the plating liquid monitoring unit 12 (see FIG. 2). Based on analyzed results from the plating liquid monitoring unit 12, the additive replenishing unit 14 (see FIG. 2) adds any insufficient additives via an additive replenishing pipe 64 to the plating liquid 16 in the plating liquid reservoir 16.

In the above embodiments, the plating apparatus is used for forming an interconnection by embedding copper in a fine interconnection groove defined in a surface of a semiconductor substrate. However, the plating apparatus may be used for other various purposes. For example, the apparatus may be used for forming bumps (protruding electrodes) on the surface of a semiconductor substrate for electrically connecting semiconductor chips and the substrate. Further, in the above embodiments, the substrate to be plated is immersed in the plating liquid. However, it is not necessary to immerse a substrate in a plating liquid, and the present invention is applicable to any type of plating apparatus as long as a plating liquid is sampled from a plating liquid reservoir and returned thereto. For example, the present invention can be applied to a plating apparatus for plating a substrate in such a state that the substrate faces upwardly, or a plating apparatus for plating a substrate in such a state that a plating liquid flows through a passage formed between the substrate and an anode.

Figure 5:
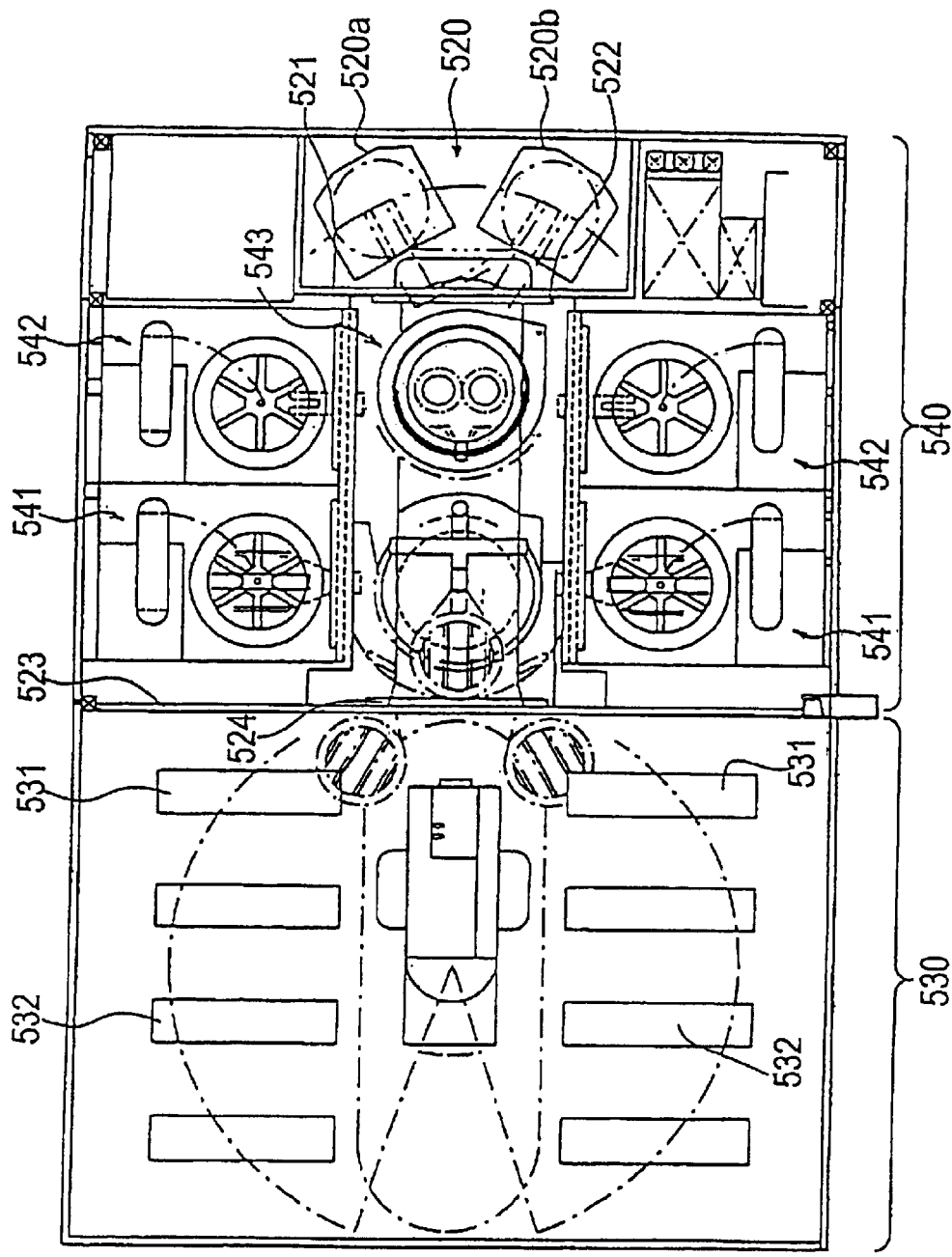
FIG. 5 is a plan view of another example of a substrate plating apparatus.

FIG. 5 is a plan view of another example of a substrate plating apparatus. The substrate plating apparatus shown in FIG. 5 comprises a loading and unloading area 520 for housing wafer cassettes which accommodate semiconductor wafers, a processing area 530 for processing semiconductor wafers, and a cleaning and drying area 540 for cleaning and drying plated semiconductor wafers. The cleaning and drying area 540 is positioned between the loading and unloading area 520, and the processing area 530. A partition 521 is disposed between the loading and unloading area 520, and the cleaning and drying area 540. A partition 523 is disposed between the cleaning and drying area 540, and the processing area 530.

The partition 521 has a passage (not shown) defined therein for transferring semiconductor wafers therethrough between the loading and unloading area 520, and the cleaning and drying area 540, and supports a shutter 522 for opening and closing the passage. The partition 523 has a passage (not shown) defined therein for transferring semiconductor wafers therethrough between the cleaning and drying area 540, and the processing area 530, and supports a shutter 524 for opening and closing the passage. Air can independently be supplied to and discharged from the cleaning and drying area 540 and the processing area 530, respectively.

The substrate plating apparatus shown in FIG. 5 is placed in a clean room, which accommodates semiconductor fabrication facilities. The pressures in the loading and unloading area 520, the processing area 530, and the cleaning and drying area 540 are selected as follows:

The pressure in the loading and unloading area 520 is greater than the pressure in the cleaning and drying area 540, which is greater than the pressure in the processing area 530.

The pressure in the loading and unloading area 520 is lower than the pressure in the clean room. Therefore, air does not flow from the processing area 530 into the cleaning and drying area 540, and air does not flow from the cleaning and drying area 540 into the loading and unloading area 520. Furthermore, air does not flow from the loading and unloading area 520 into the clean room.

The loading and unloading area 520 houses a loading unit 520a and an unloading unit 520b, each accommodating a wafer cassette for storing semiconductor wafers. The cleaning and drying area 540 houses two water cleaning units 541 for cleaning plated semiconductor wafers with water, and two drying units 542 for drying plated semiconductor wafers. Each of the water cleaning units 541 may comprise a pencil-shaped cleaner with a sponge layer mounted on a front end thereof or a roller with a sponge layer mounted on an outer circumferential surface thereof. Each of the drying units 542 may comprise a drier for spinning a semiconductor wafer at a high speed to dehydrate and dry. The cleaning and drying area 540 also has a transfer unit (transfer robot) 543 for transferring semiconductor wafers.

The processing area 530 houses a plurality of pretreatment chambers 531 for pretreating semiconductor wafers prior to being plated, and a plurality of plating chambers 532 for plating semiconductor wafers with copper. The processing area 530 also has a transfer unit (transfer robot) 543 for transferring semiconductor wafers.

Figure 6:
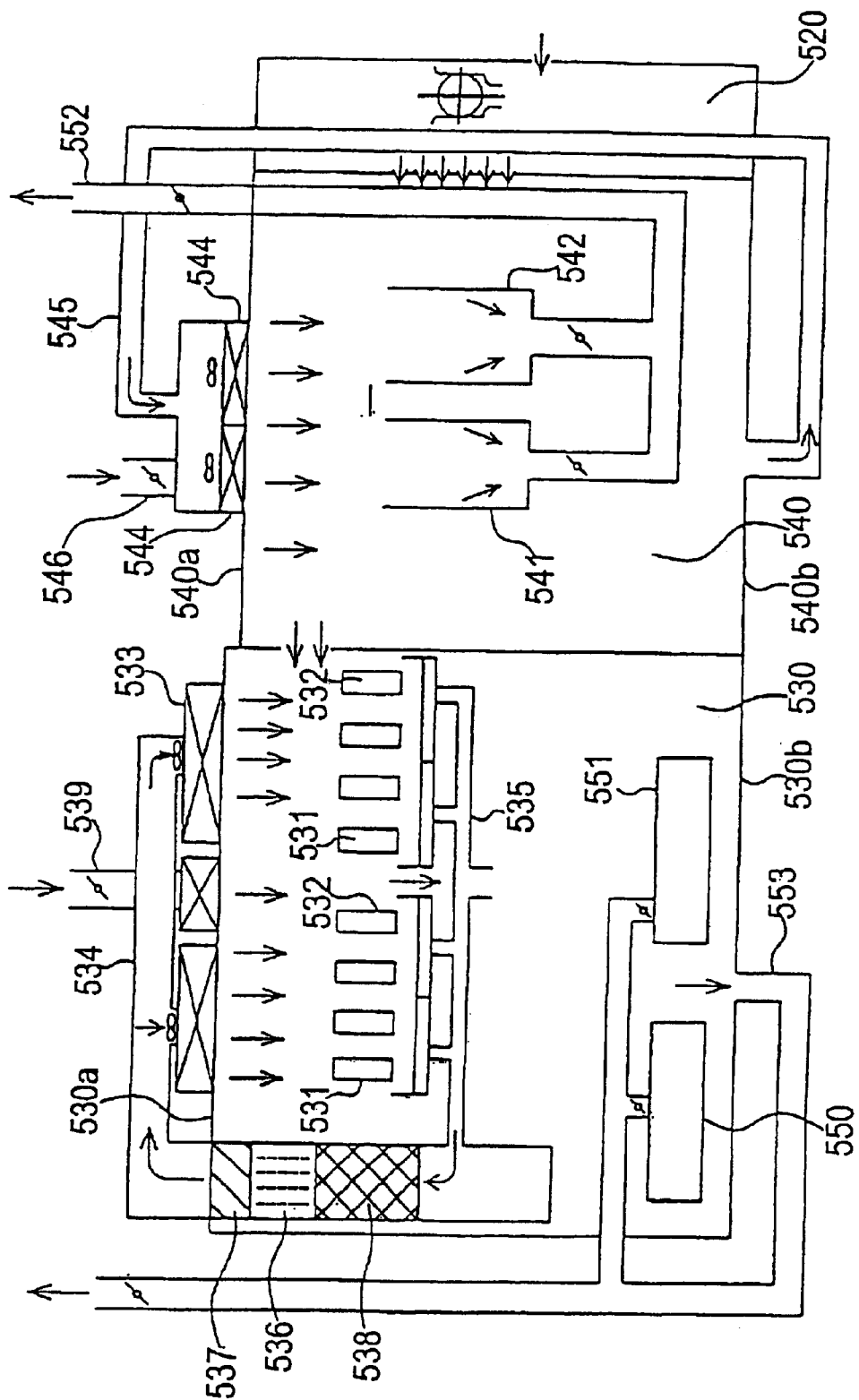
FIG. 6 is a schematic view showing airflow in the substrate plating apparatus shown in FIG. 5.

FIG. 6 shows side elevation air flows in the substrate plating apparatus. As shown in FIG. 6, fresh air is introduced from the exterior through a duct 546 and is forced through high-performance filters 544 by fans from a ceiling 540a into the cleaning and drying area 540 as downward clean air flows around the water cleaning units 541 and the drying units 542. Most of the supplied clean air is returned from a floor 540b through a circulation duct 545 to the ceiling 540a, from which the clean air is forced again through the filters 544 by the fans into the cleaning and drying area 540. Part of the clean air is discharged from the wafer cleaning units 541 and the drying units 542 through a duct 552 out of the cleaning and drying area 540.

In the processing area 530 which accommodates the pretreatment chambers 531 and the plating chambers 532, particles are not allowed to be applied to the surfaces of semiconductor wafers even though the processing area 530 is a wet zone. To prevent particles from being applied to semiconductor wafers, downward clean air flows around the pretreatment chambers 531 and the plating chambers 532. Fresh air is introduced from the exterior through a duct 539 and forced through high-performance filters 533 by fans from a ceiling 530a into the processing area 530.

If the entire amount of clean air as downward clean air flows introduced into the processing area 530 were always supplied from the exterior, then a large amount of air would be required to be introduced into and discharged from the processing area 530 at all times. According to this embodiment, air is discharged from the processing area 530 through a duct 553 at a rate sufficient enough to keep the pressure in the processing area 530 lower than the pressure in the cleaning and drying area 540, and most of the downward clean air introduced into the processing area 530 is circulated through circulation ducts 534, 535. The circulation duct 534 extends from the cleaning and drying area 540 and is connected to the filters 533 over the ceiling 530a. The circulation duct 535 is disposed in the cleaning and drying area 540 and is connected to the pipe 534 in the cleaning and drying area 540.

The circulating air that has passed through the processing area 530 contains a chemical mist and gases from solution bathes. The chemical mist and gases are removed from the circulating air by a scrubber 536 and mist separators 537, 538 which are disposed in the pipe 534 that is connected to the pipe 535. The air which circulates from the cleaning and drying area 540 through the scrubber 536 and the mist separators 537, 538 back into the circulation duct 534 over the ceiling 530a is free of any chemical mist and gases. The clean air is then forced through the filters 533 by the fans to circulate back into the processing area 530.

Part of the air is discharged from the processing area 530 through the duct 553 connected to a floor 530b of the processing area 530. Air containing a chemical mist and gases is also discharged from the processing area 530, through the duct 553. An amount of fresh air which is commensurate with the amount of air discharged through the duct 553 is supplied from the duct 539 into the plating chamber 530 under the negative pressure developed therein with respect to the pressure in the clean room.

Figure 7:
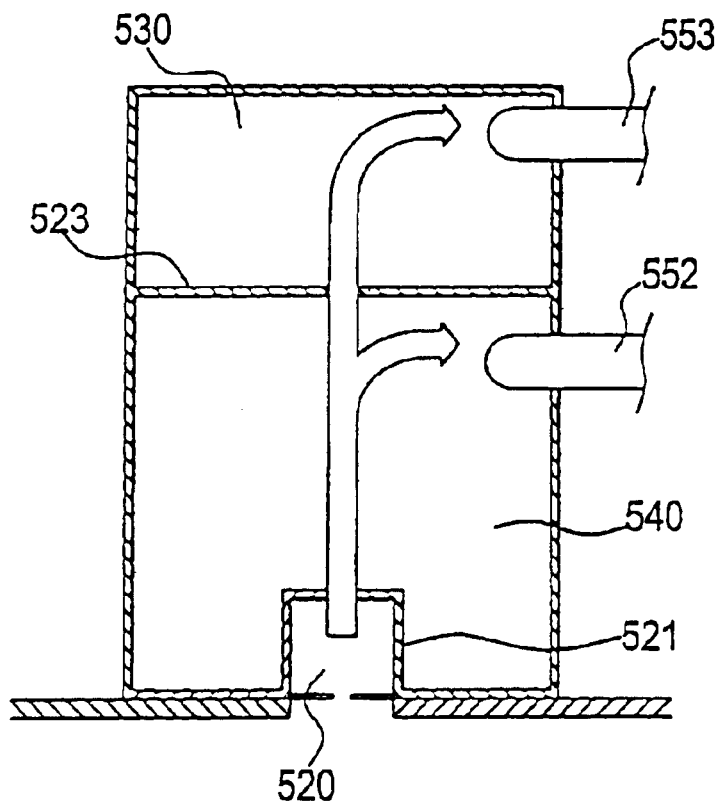
FIG. 7 is a cross-sectional view showing airflows among areas in the substrate plating apparatus shown in FIG. 5.

As described above, the pressure in the loading and unloading area 520 is higher than the pressure in the cleaning and drying area 540, which is higher than the pressure in the processing area 530. When the shutters 522, 524 (see FIG. 5) are opened, therefore, air flows successively through the loading and unloading area 520, the cleaning and drying area 540, and the processing area 530, as shown in FIG. 7. Air discharged from the cleaning and drying area 540 and the processing area 530 flows through the ducts 552, 553 into a common duct 554 (see FIG. 8) which extends out of the clean room.

Figure 8:
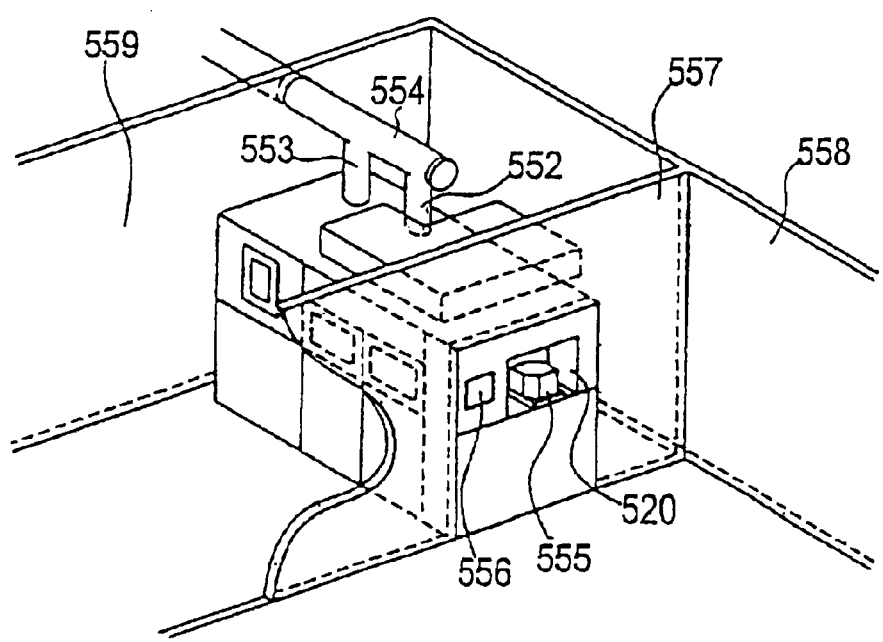
FIG. 8 is a perspective view of the substrate plating apparatus shown in FIG. 5, which is placed in a clean room.

FIG. 8 shows in perspective the substrate plating apparatus shown in FIG. 5, which is placed in the clean room. The loading and unloading area 520 includes a side wall which has a cassette transfer port 555 defined therein and a control panel 556, and which is exposed to a working zone 558 that is compartmented in the clean room by a partition wall 557. The partition wall 557 also compartments a utility zone 559 in the clean room in which the substrate plating apparatus is installed. Other sidewalls of the substrate plating apparatus are exposed to the utility zone 559, whose air cleanness is lower than the air cleanness in the working zone 558.

As described above, the cleaning and drying area 540 is disposed between the loading and unloading area 520, and the processing area 530. The partition 521 is disposed between the loading and unloading area 520, and the cleaning and drying area 540. The partition 523 is disposed between the cleaning and drying area 540, and the processing area 530. A dry semiconductor wafer is loaded from the working zone 558 through the cassette transfer port 555 into the substrate plating apparatus, and then plated in the substrate plating apparatus. The plated semiconductor wafer is cleaned and dried, and then unloaded from the substrate plating apparatus through the cassette transfer port 555 into the working zone 558. Consequently, no particles and mist are applied to the surface of the semiconductor wafer, and the working zone 558 which has higher air cleanness than the utility zone 557 is prevented from being contaminated by particles, chemical mists, and cleaning solution mists.

In the embodiment shown in FIGS. 5 and 6, the substrate plating apparatus has the loading and unloading area 520, the cleaning and drying area 540, and the processing area 530. However, an area accommodating a chemical mechanical polishing unit may be disposed in or adjacent to the processing area 530, and the cleaning and drying area 540 may be disposed in the processing area 530 or between the area accommodating the chemical mechanical polishing unit and the loading and unloading area 520. Any of various other suitable area and unit layouts may be employed insofar as a dry semiconductor wafer can be loaded into the substrate plating apparatus, and a plated semiconductor wafer can be cleaned and dried, and thereafter unloaded from the substrate plating apparatus.

In the embodiment described above, the present invention is applied to the substrate plating apparatus for plating a semiconductor wafer. However, the principles of the present invention are also applicable to a substrate plating apparatus for plating a substrate other than a semiconductor wafer. Furthermore, a region on a substrate plated by the substrate plating apparatus is not limited to an interconnection region on the substrate. The substrate plating apparatus may be used to plate substrates with a metal other than copper.

Figure 9:
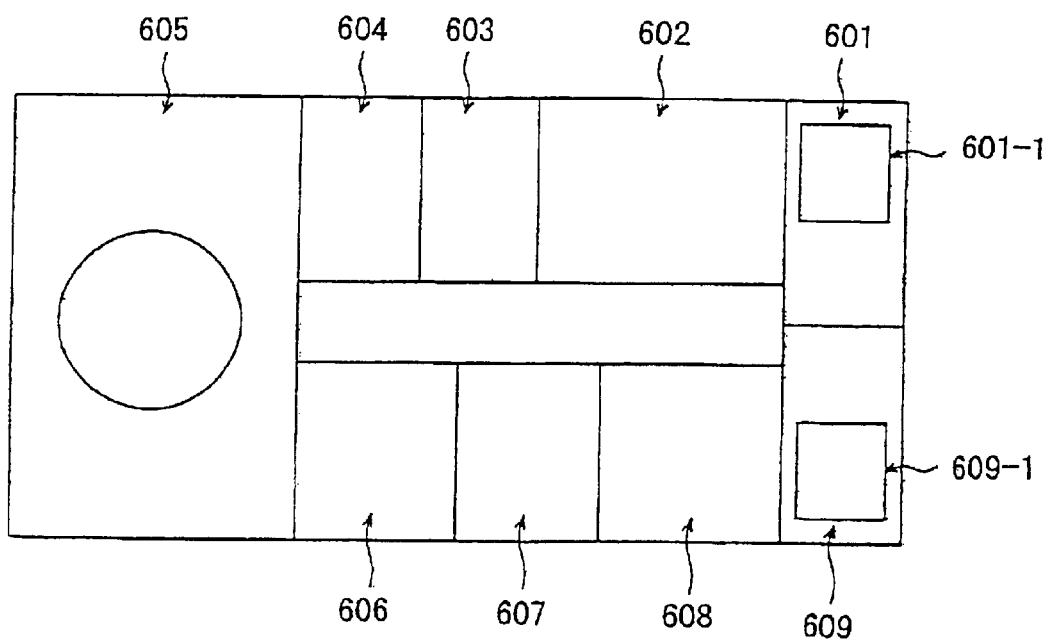
FIG. 9 is a plan view of still another example of a substrate plating apparatus.

FIG. 9 is a plan view of still another example of a substrate plating apparatus. The substrate plating apparatus shown in FIG. 9 comprises a loading unit 601 for loading a semiconductor wafer, a copper plating chamber 602 for plating a semiconductor wafer with copper, a pair of water cleaning chambers 603, 604 for cleaning a semiconductor wafer with water, a chemical mechanical polishing unit 605 for chemically and mechanically polishing a semiconductor wafer, a pair of water cleaning chambers 606, 607 for cleaning a semiconductor wafer with water, a drying chamber 608 for drying a semiconductor wafer, and an unloading unit 609 for unloading a semiconductor wafer with an interconnection film thereon. The substrate plating apparatus also has a wafer transfer mechanism (not shown) for transferring semiconductor wafers to the chambers 602, 603, 604, the chemical mechanical polishing unit 605, the chambers 606, 607, 608, and the unloading unit 609. The loading unit 601, the chambers 602, 603, 604, the chemical mechanical polishing unit 605, the chambers 606, 607, 608, and the unloading unit 609 are combined into a single unitary arrangement as an apparatus.

The substrate plating apparatus operates as follows: The wafer transfer mechanism transfers a semiconductor wafer W on which an interconnection film has not yet been formed from a wafer cassette 601-1 placed in the loading unit 601 to the copper plating chamber 602. In the copper plating chamber 602, a plated copper film is formed on a surface of the semiconductor wafer W having an interconnection region composed of an interconnection trench and an interconnection hole (contact hole).

After the plated copper film is formed on the semiconductor wafer W in the copper plating chamber 602, the semiconductor wafer W is transferred to one of the water cleaning chambers 603, 604 by the wafer transfer mechanism and cleaned by water in one of the water cleaning chambers 603, 604. The cleaned semiconductor wafer W is transferred to the chemical mechanical polishing unit 605 by the wafer transfer mechanism. The chemical mechanical polishing unit 605 removes the unwanted plated copper film from the surface of the semiconductor wafer W, leaving a portion of the plated copper film in the interconnection trench and the interconnection hole. A barrier layer made of TiN or the like is formed on the surface of the semiconductor wafer W, including the inner surfaces of the interconnection trench and the interconnection hole, before the plated copper film is deposited.

Then, the semiconductor wafer W with the remaining plated copper film is transferred to one of the water cleaning chambers 606, 607 by the wafer transfer mechanism and cleaned by water in one of the water cleaning chambers 607, 608. The cleaned semiconductor wafer W is then dried in the drying chamber 608, after which the dried semiconductor wafer W with the remaining plated copper film serving as an interconnection film is placed into a wafer cassette 609-1 in the unloading unit 609.

Figure 10:
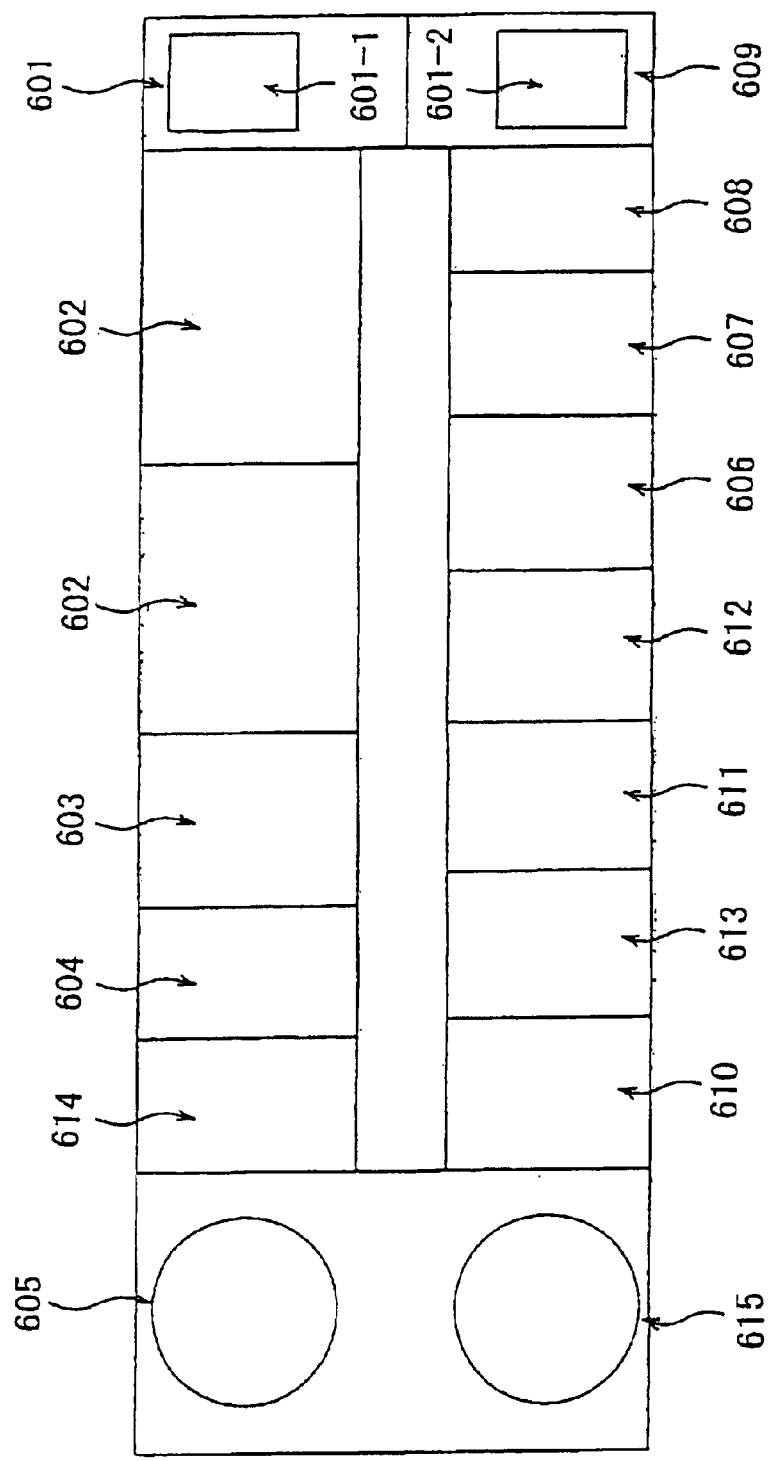
FIG. 10 is a plan view of still another example of a substrate plating apparatus.

FIG. 10 shows a plan view of still another example of a substrate plating apparatus. The substrate plating apparatus shown in FIG. 10 differs from the substrate plating apparatus shown in FIG. 9 in that it additionally includes a copper plating chamber 602, a water cleaning chamber 610, a pretreatment chamber 611, a protective layer plating chamber 612 for forming a protective plated layer on a plated copper film on a semiconductor wafer, water cleaning chamber 613, 614, and a chemical mechanical polishing unit 615. The loading unit 601, the chambers 602, 602, 603, 604, 614, the chemical mechanical polishing unit 605, 615, the chambers 606, 607, 608, 610, 611, 612, 613, and the unloading unit 609 are combined into a single unitary arrangement as an apparatus.

The substrate plating apparatus shown in FIG. 10 operates as follows: A semiconductor wafer W is supplied from the wafer cassette 601-1 placed in the loading unit 601 successively to one of the copper plating chambers 602, 602. In one of the copper plating chambers 602, 602, a plated copper film is formed on a surface of a semiconductor wafer W having an interconnection region composed of an interconnection trench and an interconnection hole (contact hole). The two copper plating chambers 602, 602 are employed to allow the semiconductor wafer W to be plated with a copper film for a long period of time. Specifically, the semiconductor wafer W may be plated with a primary copper film according to electroplating in one of the copper plating chamber 602, and then plated with a secondary copper film according to electroless plating in the other copper plating chamber 602. The substrate plating apparatus may have more than two copper plating chambers.

The semiconductor wafer W with the plated copper film formed thereon is cleaned by water in one of the water cleaning chambers 603, 604. Then, the chemical mechanical polishing unit 605 removes the unwanted portion of the plated copper film from the surface of the semiconductor wafer W, leaving a portion of the plated copper film in the interconnection trench and the interconnection hole.

Thereafter, the semiconductor wafer W with the remaining plated copper film is transferred to the water cleaning chamber 610, in which the semiconductor wafer W is cleaned with water. Then, the semiconductor wafer W is transferred to the pretreatment chamber 611, and pretreated therein for the deposition of a protective plated layer. The pretreated semiconductor wafer W is transferred to the protective layer-plating chamber 612. In the protective layer plating chamber 612, a protective plated layer is formed on the plated copper film in the interconnection region on the semiconductor wafer W. For example, the protective plated layer is formed with an alloy of nickel (Ni) and boron (B) by electroless plating.

After the semiconductor wafer is cleaned in one of the water cleaning chambers 613, 614, an upper portion of the protective plated layer deposited on the plated copper film is polished off to planarize the protective plated layer, in the chemical mechanical polishing unit 615.

After the protective plated layer is polished, the semiconductor wafer W is cleaned by water in one of the water cleaning chambers 606, 607, dried in the drying chamber 608, and then transferred to the wafer cassette 609-1 in the unloading unit 609.

Figure 11:
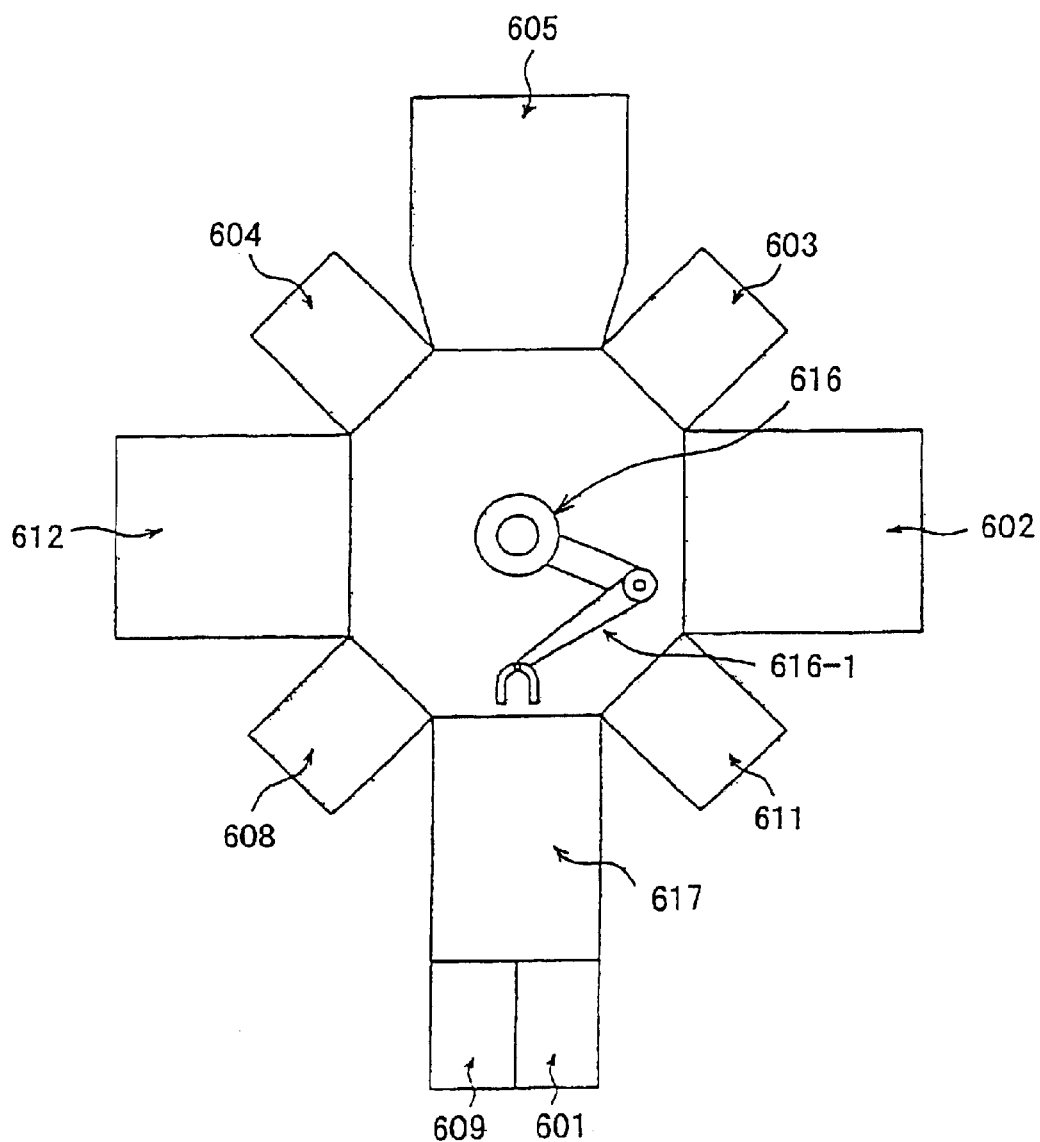
FIG. 11 is a plan view of still another example of a substrate plating apparatus.

FIG. 11 is a plan view of still another example of a substrate plating apparatus. As shown in FIG. 11, the substrate plating apparatus includes a robot 616 at its center which has a robot arm 616-1, and also has a copper plating chamber 602, a pair of water cleaning chambers 603, 604, a chemical mechanical polishing unit 605, a pretreatment chamber 611, a protective layer plating chamber 612, a drying chamber 608, and a loading and unloading station 617 which are disposed around the robot 616 and positioned within the reach of the robot arm 616-1. A loading unit 601 for loading semiconductor wafers and an unloading unit 609 for unloading semiconductor wafers is disposed adjacent to the loading and unloading station 617. The robot 616, the chambers 602, 603, 604, the chemical mechanical polishing unit 605, the chambers 608, 611, 612, the loading and unloading station 617, the loading unit 601, and the unloading unit 609 are combined into a single unitary arrangement as an apparatus.

The substrate plating apparatus shown in FIG. 11 operates as follows:

A semiconductor wafer to be plated is transferred from the loading unit 601 to the loading and unloading station 617, from which the semiconductor wafer is received by the robot arm 616-1 and transferred thereby to the copper plating chamber 602. In the copper plating chamber 602, a plated copper film is formed on a surface of the semiconductor wafer which has an interconnection region composed of an interconnection trench and an interconnection hole. The semiconductor wafer with the plated copper film formed thereon is transferred by the robot arm 616-1 to the chemical mechanical polishing unit 605. In the chemical mechanical polishing unit 605, the plated copper film is removed from the surface of the semiconductor wafer W, leaving a portion of the plated copper film in the interconnection trench and the interconnection hole.

The semiconductor wafer is then transferred by the robot arm 616-1 to the water-cleaning chamber 604, in which the semiconductor wafer is cleaned by water. Thereafter, the semiconductor wafer is transferred by the robot arm 616-1 to the pretreatment chamber 611, in which the semiconductor wafer is pretreated therein for the deposition of a protective plated layer. The pretreated semiconductor wafer is transferred by the robot arm 616-1 to the protective layer plating chamber 612. In the protective layer plating chamber 612, a protective plated layer is formed on the plated copper film in the interconnection region on the semiconductor wafer W. The semiconductor wafer with the protective plated layer formed thereon is transferred by the robot arm 616-1 to the water cleaning chamber 604, in which the semiconductor wafer is cleaned by water. The cleaned semiconductor wafer is transferred by the robot arm 616-1 to the drying chamber 608, in which the semiconductor wafer is dried. The dried semiconductor wafer is transferred by the robot arm 616-1 to the loading and unloading station 617, from which the plated semiconductor wafer is transferred to the unloading unit 609.

Figure 12:
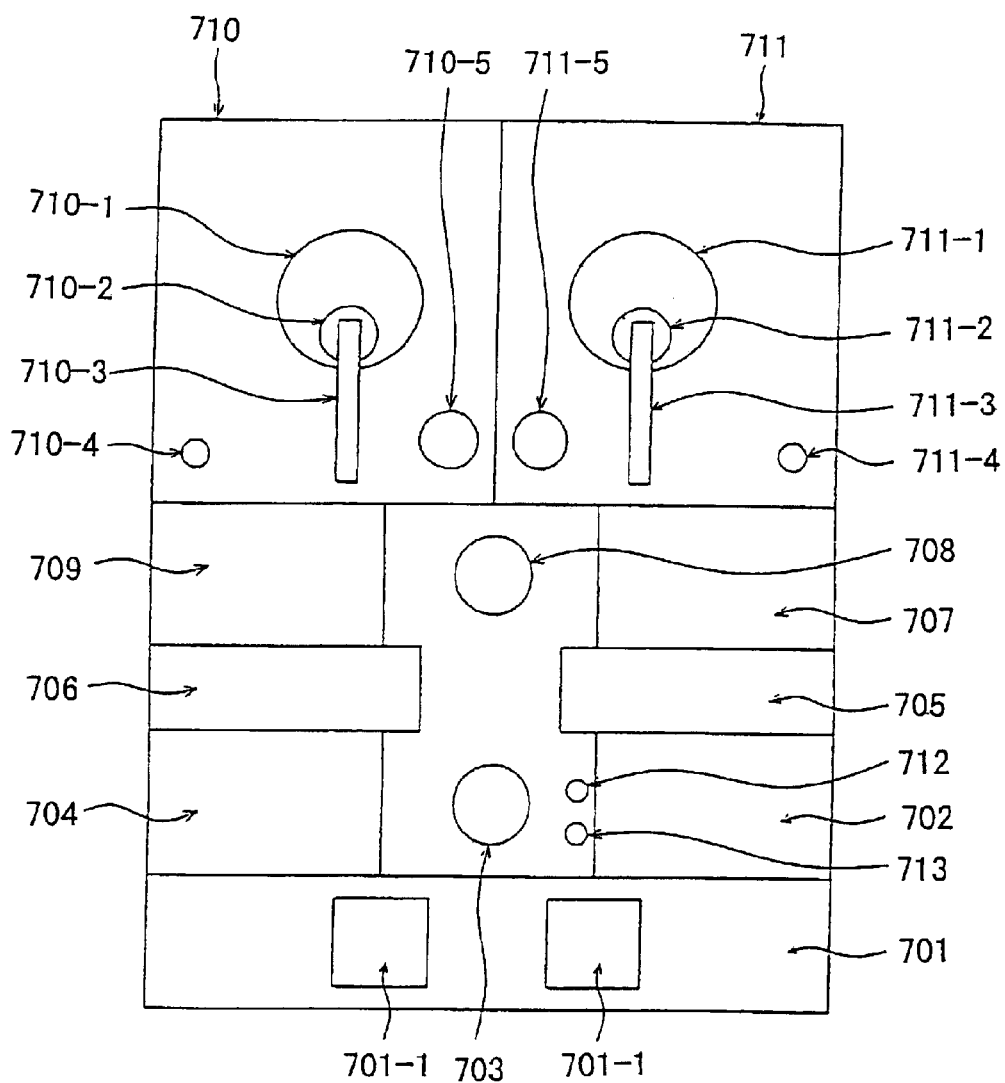
FIG. 12 is a view showing a plan constitution example of the semiconductor substrate processing apparatus.

FIG. 12 is a plan view of another example of a semiconductor substrate processing apparatus. The semiconductor substrate processing apparatus includes a loading and unloading section 701, a plated Cu film forming unit 702, a first robot 703, a third cleaning machine 704, a reversing machine 705, a reversing machine 706, a second cleaning machine 707, a second robot 708, a first cleaning machine 709, a first polishing apparatus 710, and a second polishing apparatus 711. A before-plating and after-plating film thickness measuring instrument 712 for measuring the film thicknesses before and after plating, and a dry state film thickness measuring instrument 713 for measuring the film thickness of a semiconductor substrate W in a dry state after polishing are placed near the first robot 703.

The first polishing apparatus (polishing unit) 710 has a polishing table 710-1, a top ring 710-2, a top ring head 710-3, a film thickness measuring instrument 710-4, and a pusher 710-5. The second polishing apparatus (polishing unit) 711 has a polishing table 711-1, a top ring 711-2, a top ring head 711-3, a film thickness measuring instrument 711-4, and a pusher 711-5.

A cassette 701-1 accommodating the semiconductor substrates W, in which a via hole and a trench for interconnect are formed, and a seed layer is formed thereon is placed on a loading port of the loading and unloading section 701. The first robot 703 takes out the semiconductor substrate W from the cassette 701-1, and carries the semiconductor substrate W into the plated Cu film forming unit 702 where a plated Cu film 106 is formed. At this time, the film thickness of the seed layer is measured with the before-plating and after-plating film thickness measuring instrument 712. The plated Cu film is formed by carrying out hydrophilic treatment of the face of the semiconductor substrate W, and then Cu plating. After formation of the plated Cu film, rinsing or cleaning of the semiconductor substrate W is carried out in the plated Cu film forming unit 702.

When the semiconductor substrate W is taken out from the plated Cu film forming unit 702 by the first robot 703, the film thickness of the plated Cu film is measured with the before-plating and after-plating film thickness measuring instrument 712. The results of its measurement are recorded by a recording device (not shown) as record data on the semiconductor substrate, and are used to determine any abnormality of the plated Cu film forming unit 702. After measurement of the film thickness, the first robot 703 transfers the semiconductor substrate W to the reversing machine 705, and the reversing machine 705 reverses the semiconductor substrate W (the surface on which the plated Cu film has been formed faces downward). The first polishing apparatus 710 and the second polishing apparatus 711 perform polishing in a serial mode and a parallel mode. Next, polishing in the serial mode will be described.

In the serial mode polishing, a primary polishing is performed by the polishing apparatus 710, and a secondary polishing is performed by the polishing apparatus 711. The second robot 708 picks up the semiconductor substrate W on the reversing machine 705, and places the semiconductor substrate W on the pusher 710-5 of the polishing apparatus 710. The top ring 710-2 attracts the semiconductor substrate W on the pusher 710-5 by suction, and brings the surface of the plated Cu film of the semiconductor substrate W into contact with a polishing surface of the polishing table 710-1 under pressure to perform a primary polishing. With the primary polishing, the plated Cu film is basically polished. The polishing surface of the polishing table 710-1 is composed of foamed polyrethane such as IC1000, or a material having abrasive grains fixed thereto or impregnated therein. Upon relative movements of the polishing surface and the semiconductor substrate W, the plated Cu film is polished.

After completion of polishing of the plated Cu film, the semiconductor substrate W is returned onto the pusher 710-5 by the top ring 710-2. The second robot 708 picks up the semiconductor substrate W, and introduces it into the first cleaning machine 709. At this time, a chemical liquid may be ejected toward the face and backside of the semiconductor substrate W on the pusher 710-5 to remove particles therefrom or make it difficult for particles to adhere thereto.

After completion of cleaning in the first cleaning machine 709, the second robot 708 picks up the semiconductor substrate W, and places the semiconductor substrate W on the pusher 711-5 of the second polishing apparatus 711. The top ring 711-2 attracts the semiconductor substrate W on the pusher 711-5 by suction, and brings the surface of the semiconductor substrate W, which has the barrier layer formed thereon, into contact with a polishing surface of the polishing table 711-1 under pressure to perform the secondary polishing. The constitution of the polishing table is the same as the top ring 711-2. With this secondary polishing, the barrier layer is polished. However, there may be a case in which a Cu film and an oxide film left after the primary polishing are also polished.

A polishing surface of the polishing table 711-1 is composed of foamed polyrethane such as IC1000, or a material having abrasive grains fixed thereto or impregnated therein. Upon relative movements of the polishing surface and the semiconductor substrate W, polishing is carried out. At this time, silica, alumina, ceria, on the like is used as abrasive grains or a slurry. A chemical liquid is adjusted depending on the type of the film to be polished.

Detection of an end point of the secondary polishing is performed by measuring the film thickness of the barrier layer mainly with the use of the optical film thickness measuring instrument, and detecting the film thickness which has become zero, or the surface of an insulating film comprising SiO2 shows up. Furthermore, a film thickness measuring instrument with an image processing function is used as the film thickness measuring instrument 711-4 provided near the polishing table 711-1. By use of this measuring instrument, measurement of the oxide film is made, the results are stored as processing records of the semiconductor substrate W, and are used for judging whether the semiconductor substrate W in which secondary polishing has been finished can be transferred to a subsequent step or not. If the end point of the secondary polishing is not reached, repolishing is performed. If over-polishing has been performed beyond a prescribed value due to any abnormality, then the semiconductor substrate processing apparatus is stopped to avoid further polishing so that defective products will not increase.

After completion of the secondary polishing, the semiconductor substrate W is moved to the pusher 711-5 by the top ring 711-2. The second robot 708 picks up the semiconductor substrate W on the pusher 711-5. At this time, a chemical liquid may be ejected toward the face and backside of the semiconductor substrate W on the pusher 711-5 to remove particles therefrom or make it difficult for particles to adhere thereto.

The second robot 708 carries the semiconductor substrate W into the second cleaning machine 707 where cleaning of the semiconductor substrate W is performed. The constitution of the second cleaning machine 707 is also the same as the constitution of the first cleaning machine 709. The face of the semiconductor substrate W is scrubbed with the PVA sponge rolls using a cleaning liquid comprising pure water to which a surface active agent, a chelating agent, or a pH regulating agent is added. A strong chemical liquid such as DHEF is ejected from a nozzle toward the backside of the semiconductor substrate W to perform etching of the diffused Cu thereon. If there is no problem of diffusion, scrubbing cleaning is performed with the PVA sponge rolls using the same chemical liquid as that used for the face.

After completion of the above cleaning, the second robot 708 picks up the semiconductor substrate W and transfers it to the reversing machine 706, and the reversing machine 706 reverses the semiconductor substrate W. The semiconductor substrate W which has been reversed is picked up by the first robot 703, and transferred to the third cleaning machine 704. In the third cleaning machine 704, megasonic water excited by ultrasonic vibrations is ejected toward the face of the semiconductor substrate W to clean the semiconductor substrate W. At this time, the face of the semiconductor substrate W may be cleaned with a known pencil type sponge using a cleaning liquid comprising pure water to which a surface active agent, a chelating agent, or a pH regulating agent is added. Thereafter, the semiconductor substrate W is dried by spin-drying.

As described above, if the film thickness has been measured with the film thickness measuring instrument 711-4 provided near the polishing table 711-1, then the semiconductor substrate W is not subjected to further processing, and is placed into the cassette placed on the unloading port of the loading and unloading section 771.

Figure 13:
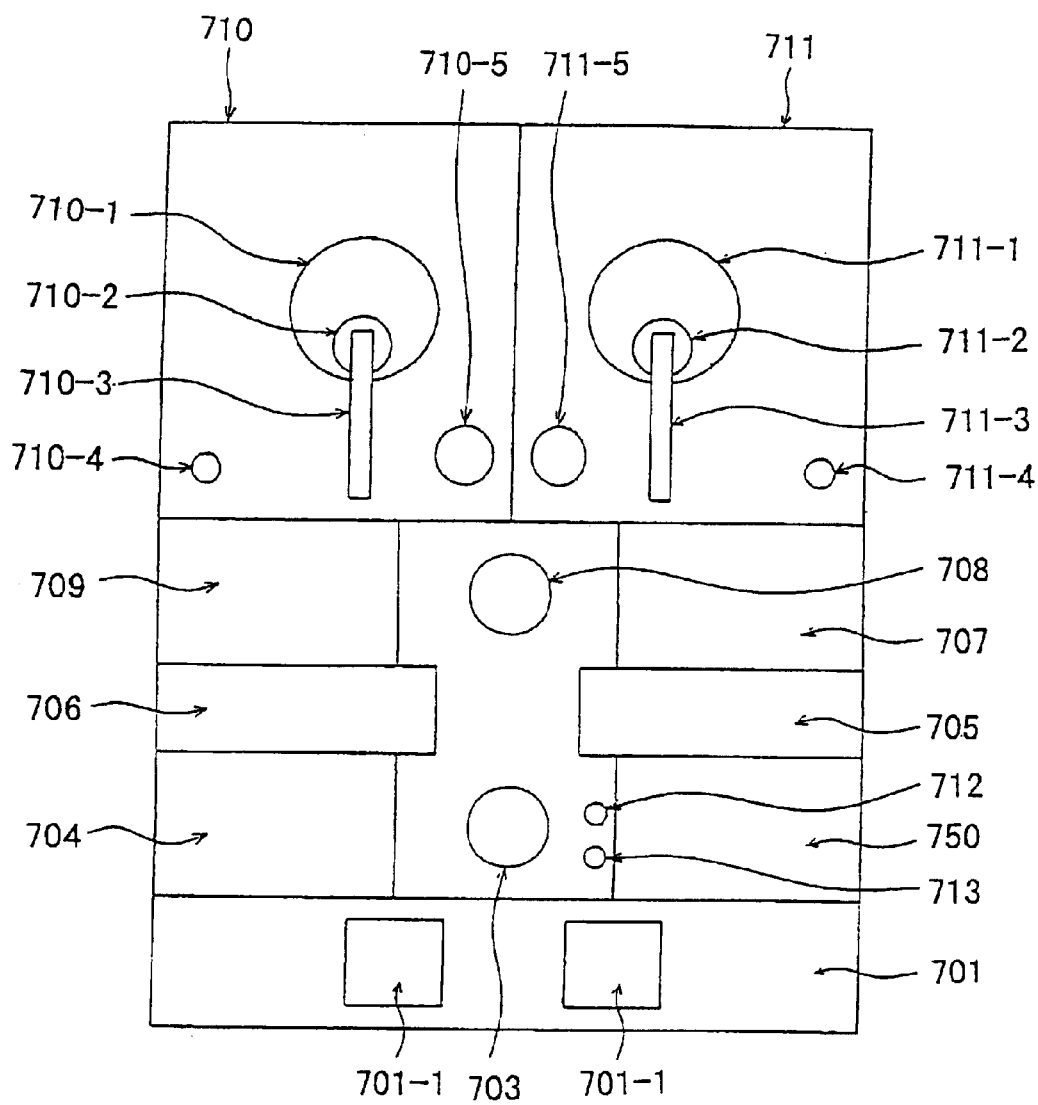
FIG. 13 is a plan view showing another example of the semiconductor substrate processing apparatus.

FIG. 13 is a plan view showing another example of a semiconductor substrate processing apparatus. The substrate processing apparatus differs from the substrate processing apparatus shown in FIG. 12 in that a cap plating unit 750 is provided instead of the plated Cu film forming unit 702 in FIG. 12.

A cassette 701-1 accommodating the semiconductor substrates W plated with the Cu film is placed on a load port of a loading and unloading section 701. The semiconductor substrate W taken out from the cassette 701-1 is transferred to the first polishing apparatus 710 or second polishing apparatus 711, in which the surface of the plated Cu film is polished. After completion of the polishing of the plated Cu film, the semiconductor substrate W is cleaned in the first cleaning machine 709.

After completion of cleaning in the first cleaning machine 709, the semiconductor substrate W is transferred to the cap plating unit 750 where cap plating is applied onto the surface of the plated Cu film with the aim of preventing oxidation of plated Cu film due to the atmosphere. The semiconductor substrate to which cap plating has been applied is carried by the second robot 708 from the cap plating unit 750 to the second cleaning unit 707 where it is cleaned with pure water or deionized water. The semiconductor substrate after completion of cleaning is returned into the cassette 701-1 placed on the loading and unloading section 701.

Figure 14:
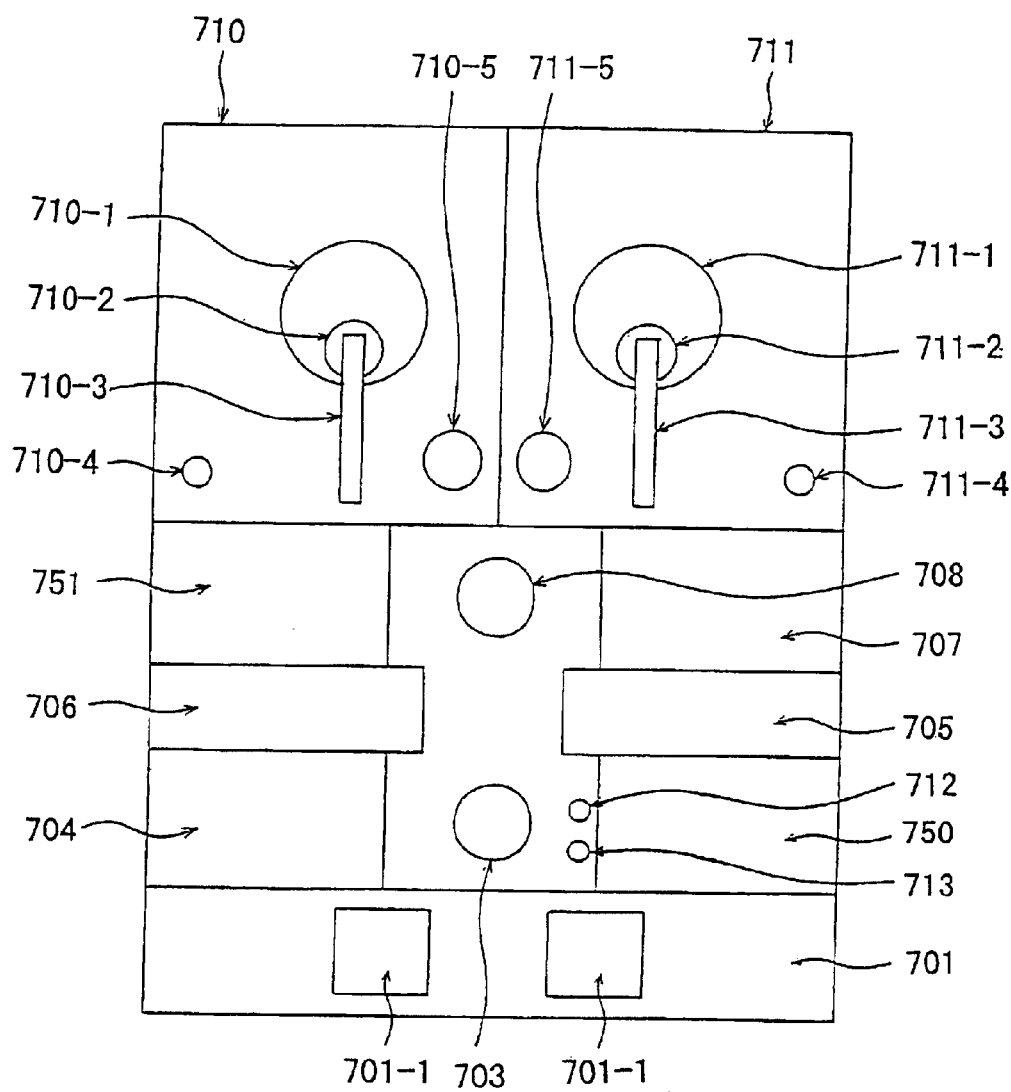
FIG. 14 is a plan view showing still another example of the semiconductor substrate processing apparatus.

FIG. 14 is a plan view showing still another example of a semiconductor substrate processing apparatus. The substrate processing apparatus differs from the substrate processing apparatus shown in FIG. 13 in that an annealing unit 751 is provided instead of the third cleaning machine 709 in FIG. 13.

The semiconductor substrate W, which is polished in the polishing unit 710 or 711, and cleaned in the first cleaning machine 709 described above, is transferred to the cap plating unit 750 where cap plating is applied onto the surface of the plated Cu film. The semiconductor substrate to which cap plating has been applied is carried by the second robot 132 from the cap plating unit 750 to the first cleaning unit 707 where it is cleaned.

After completion of cleaning in the first cleaning machine 709, the semiconductor substrate W is transferred to the annealing unit 751 in which the substrate is annealed, whereby the plated Cu film is alloyed so as to increase the electromigration resistance of the plated Cu film. The semiconductor substrate W to which annealing treatment has been applied is carried from the annealing unit 751 to the second cleaning unit 707 where it is cleaned with pure water or deionized water. The semiconductor substrate W after completion of cleaning is returned into the cassette 701-1 placed on the loading and unloading section 701.

Figure 15:
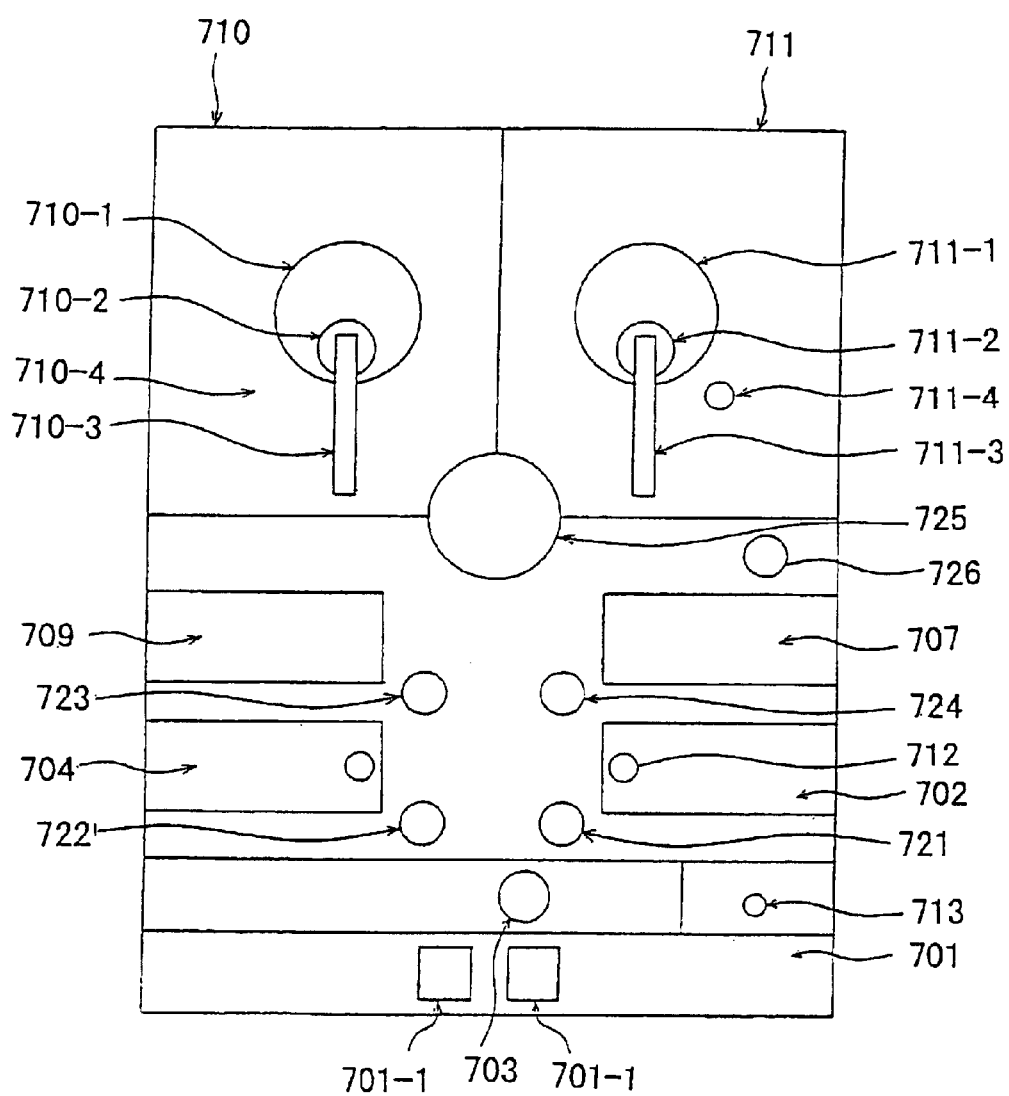
FIG. 15 is a plan view showing still another example of the semiconductor substrate processing apparatus.

FIG. 15 is a plan view of another example of the substrate processing apparatus. In FIG. 15, portions denoted by the same reference numerals as those in FIG. 12 show the same or corresponding portions. In the substrate processing apparatus, a pusher indexer 725 is disposed close to a first polishing apparatus 710 and a second polishing apparatus 711. Substrate placing tables 721, 722 are disposed close to a third cleaning machine 704 and a plated Cu film forming unit 702, respectively. A robot 23 is disposed close to a first cleaning machine 709 and the third cleaning machine 704. Further, a robot 724 is disposed close to a second cleaning machine 707 and the plated Cu film forming unit 702, and a dry state film thickness measuring instrument 713 is disposed close to a loading and unloading section 701 and a first robot 703.

In the substrate processing apparatus of the above constitution, the first robot 703 takes out a semiconductor substrate W from a cassette 701-1 placed on the load port of the loading and unloading section 701. After the film thicknesses of a barrier layer and a seed layer are measured with the dry state film thickness measuring instrument 713, the first robot 703 places the semiconductor substrate W on the substrate placing table 721. In the case where the dry state film thickness measuring instrument 713 is provided on the hand of the first robot 703, the film thicknesses are measured thereon, and the substrate is placed on the substrate placing table 72 1. The second robot 723 transfers the semiconductor substrate W on the substrate placing table 721 to the plated Cu film forming unit 702 in which a plated Cu film is formed. After formation of the plated Cu film, the film thickness of the plated Cu film is measured with a before-plating and after-plating film thickness measuring instrument 712. Then, the second robot 723 transfers the semiconductor substrate W to the pusher indexer 725 and loads it thereon.

[Serial Mode]

In the serial mode, a top ring head 710-2 holds the semiconductor substrate W on the pusher indexer 725 by suction, transfers it to a polishing table 710-1, and presses the semiconductor substrate W against a polishing surface on the polishing table 710-1 to perform polishing. Detection of the end point of polishing is performed by the same method as described above. The semiconductor substrate W after completion of polishing is transferred to the pusher indexer 725 by the top ring head 710-2, and loaded thereon. The second robot 723 takes out the semiconductor substrate W, and carries it into the first cleaning machine 709 for cleaning. Then, the semiconductor substrate W is transferred to the pusher indexer 725, and loaded thereon.

A top ring head 711-2 holds the semiconductor substrate W on the pusher indexer 725 by suction, transfers it to a polishing table 711-1, and presses the semiconductor substrate W against a polishing surface on the polishing table 711-1 to perform polishing. Detection of the end point of polishing is performed by the same method as described above. The semiconductor substrate W after completion of polishing is transferred to the pusher indexer 725 by the top ring head 711-2, and loaded thereon. The third robot 724 picks up the semiconductor substrate W, and its film thickness is measured with a film thickness measuring instrument 726. Then, the semiconductor substrate W is carried into the second cleaning machine 707 for cleaning. Thereafter, the semiconductor substrate W is carried into the third cleaning machine 704, where it is cleaned and then dried by spin-drying. Then, the semiconductor substrate W is picked up by the third robot 724, and placed on the substrate placing table 722.

[Parallel Mode]

In the parallel mode, the top ring head 710-2 or 711-2 holds the semiconductor substrate W on the pusher indexer 725 by suction, transfers it to the polishing table 710-1 or 711-1, and presses the semiconductor substrate W against the polishing surface on the polishing table 710-1 or 711-1 to perform polishing. After measurement of the film thickness, the third robot 724 picks up the semiconductor substrate W, and places it on the substrate placing table 722.

The first robot 703 transfers the semiconductor substrate W on the substrate placing table 722 to the dry state film thickness measuring instrument 713. After the film thickness is measured, the semiconductor substrate W is returned to the cassette 701-1 of the loading and unloading section 701.

Figure 16:
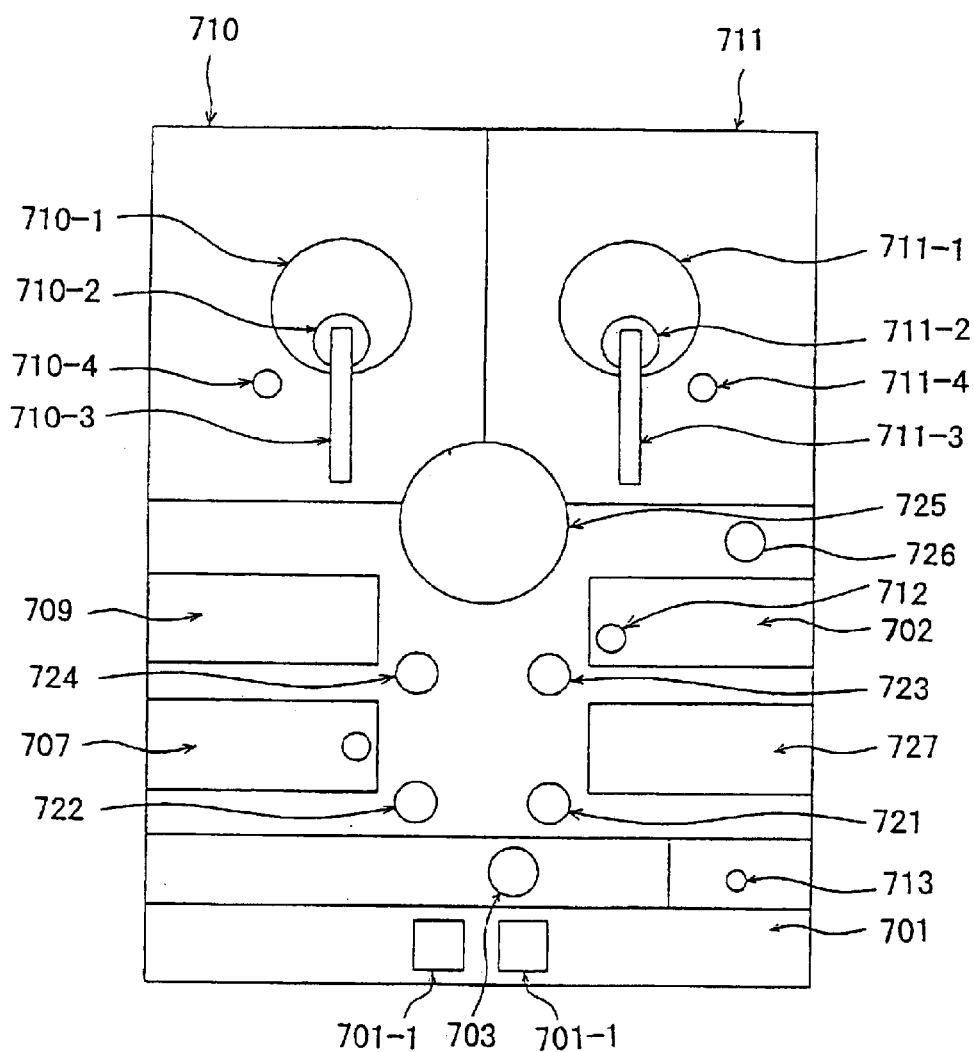
FIG. 16 is a plan view showing still another example of the semiconductor substrate processing apparatus.

FIG. 16 is a plan view showing another example of the substrate processing apparatus. The substrate processing apparatus is such a substrate processing apparatus which forms a seed layer and a plated Cu film on a semiconductor substrate W having no seed layer formed thereon, and polishes these films to form interconnects.

In the substrate polishing apparatus, a pusher indexer 725 is disposed close to a first polishing apparatus 710 and a second polishing apparatus 711, substrate placing tables 721, 722 are disposed close to a second cleaning machine 707 and a seed layer forming unit 727, respectively, and a robot 723 is disposed close to the seed layer forming unit 727 and a plated Cu film forming unit 702. Further, a robot 724 is disposed close to a first cleaning machine 709 and the second cleaning machine 707, and a dry state film thickness measuring instrument 713 is disposed close to a loading and unloading section 701 and a first robot 702.

The first robot 703 takes out a semiconductor substrate W having a barrier layer thereon from a cassette 701-1 placed on the load port of the loading and unloading section 701, and places it on the substrate placing table 721. Then, the second robot 723 transports the semiconductor substrate W to the seed layer forming unit 727 where a seed layer is formed. The seed layer is formed by electroless plating. The second robot 723 enables the semiconductor substrate having the seed layer formed thereon to have the thickness of the seed layer measured by the before-plating and after-plating film thickness measuring instrument 712. After measurement of the film thickness, the semiconductor substrate is carried into the plated Cu film forming unit 702 where a plated Cu film is formed.

After formation of the plated Cu film, its film thickness is measured, and the semiconductor substrate is transferred to a pusher indexer 725. A top ring 710-2 or 711-2 holds the semiconductor substrate W on the pusher indexer 725 by suction, and transfers it to a polishing table 710-1 or 711-1 to perform polishing. After polishing, the top ring 710-2 or 711-2 transfers the semiconductor substrate W to a film thickness measuring instrument 7104 or 711-4 to measure the film thickness. Then, the top ring 710-2 or 711-2 transfers the semiconductor substrate W to the pusher indexer 725, and places it thereon.

Then, the third robot 724 picks up the semiconductor substrate W from the pusher indexer 725, and carries it into the first cleaning machine 709. The third robot 724 picks up the cleaned semiconductor substrate W from the first cleaning machine 709, carries it into the second cleaning machine 707, and places the cleaned and dried semiconductor substrate on the substrate placing table 722. Then, the first robot 703 picks up the semiconductor substrate W, and transfers it to the dry state film thickness measuring instrument 713 in which the film thickness is measured, and the first robot 703 carries it into the cassette 701-1 placed on the unload port of the loading and unloading section 701.

In the substrate processing apparatus shown in FIG. 16, interconnects are formed by forming a barrier layer, a seed layer and a plated Cu film on a semiconductor substrate W having a via hole or a trench of a circuit pattern formed therein, and polishing them.

The cassette 701-1 accommodating the semiconductor substrates W before formation of the barrier layer is placed on the load port of the loading and unloading section 701. The first robot 703 takes out the semiconductor substrate W from the cassette 701-1 placed on the load port of the loading and unloading section 701, and places it on the substrate placing table 721. Then, the second robot 723 transports the semiconductor substrate W to the seed layer forming unit 727 where a barrier layer and a seed layer are formed. The barrier layer and the seed layer are formed by electroless plating. The second robot 723 brings the semiconductor substrate W having the barrier layer and the seed layer formed thereon to the before-plating and after-plating film thickness measuring instrument 712 which measures the film thicknesses of the barrier layer and the seed layer. After measurement of the film thicknesses, the semiconductor substrate W is carried into the plated Cu film forming unit 702 where a plated Cu film is formed.

Figure 17:
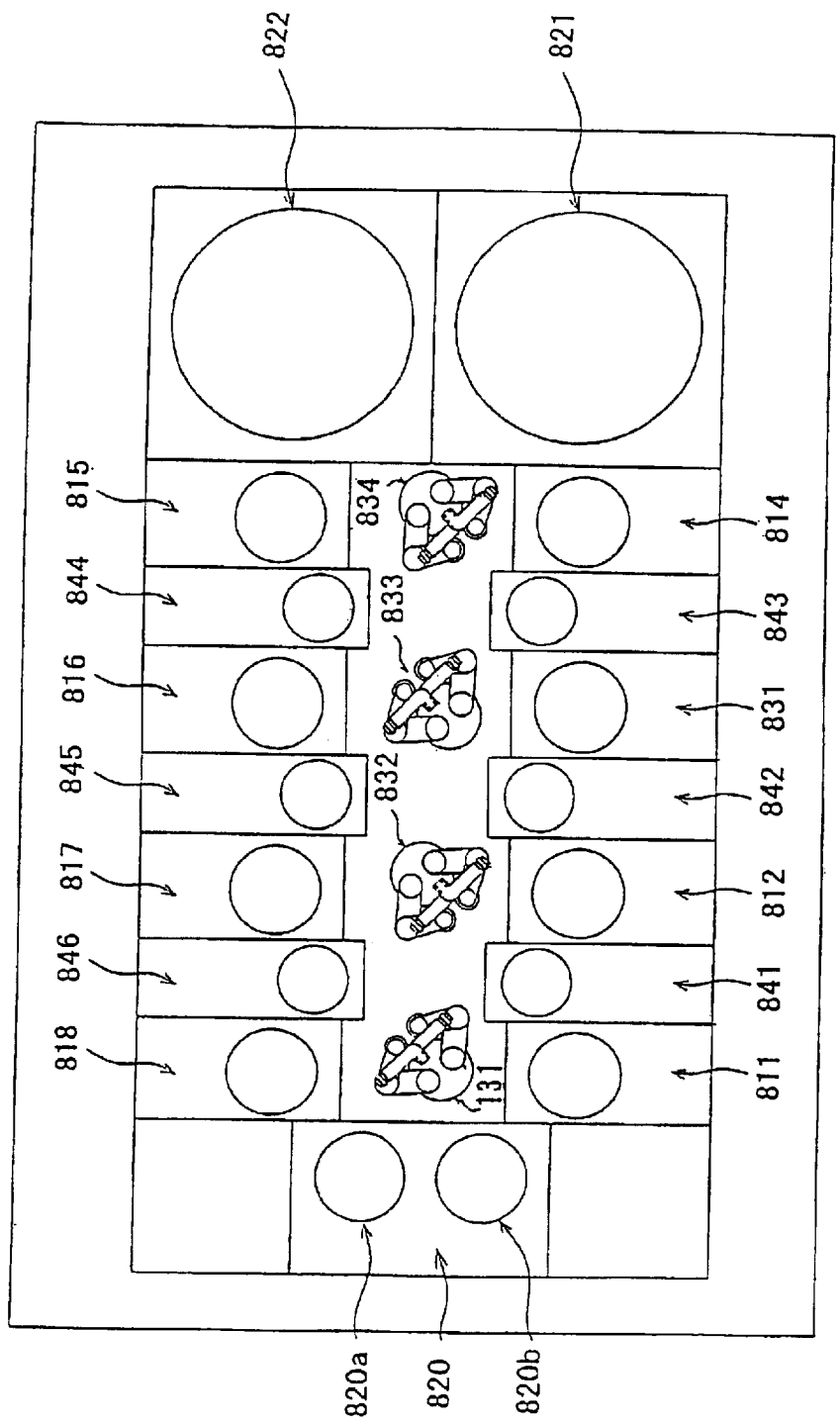
FIG. 17 is a plan view showing still another example of the semiconductor substrate processing apparatus.

FIG. 17 is a plan view showing another example of the substrate processing apparatus. In the substrate processing apparatus, there are provided a barrier layer forming unit 811, a seed layer forming unit 812, a plated film forming unit 813, an annealing unit 814, a first cleaning unit 815, a bevel and backside cleaning unit 816, a cap plating unit 817, a second cleaning unit 818, a first aligner and film thickness measuring instrument 841, a second aligner and film-thickness measuring instrument 842, a first substrate reversing machine 843, a second substrate reversing machine 844, a substrate temporary placing table 845, a third film thickness measuring instrument 846, a loading and unloading section 820, a first polishing apparatus 821, a second polishing apparatus 822, a first robot 831, a second robot 832, a third robot 833, and a fourth robot 834. The film thickness measuring instruments 841, 842, and 846 are units, have the same size as the frontage dimension of other units (plating, cleaning, annealing units, and the like), and are thus interchangeable.

In this example, an electroless Ru plating apparatus can be used as the barrier layer forming unit 811, an electroless Cu plating apparatus as the seed layer forming unit 812, and an electroplating apparatus as the plated film forming unit 813.

Figure 18:
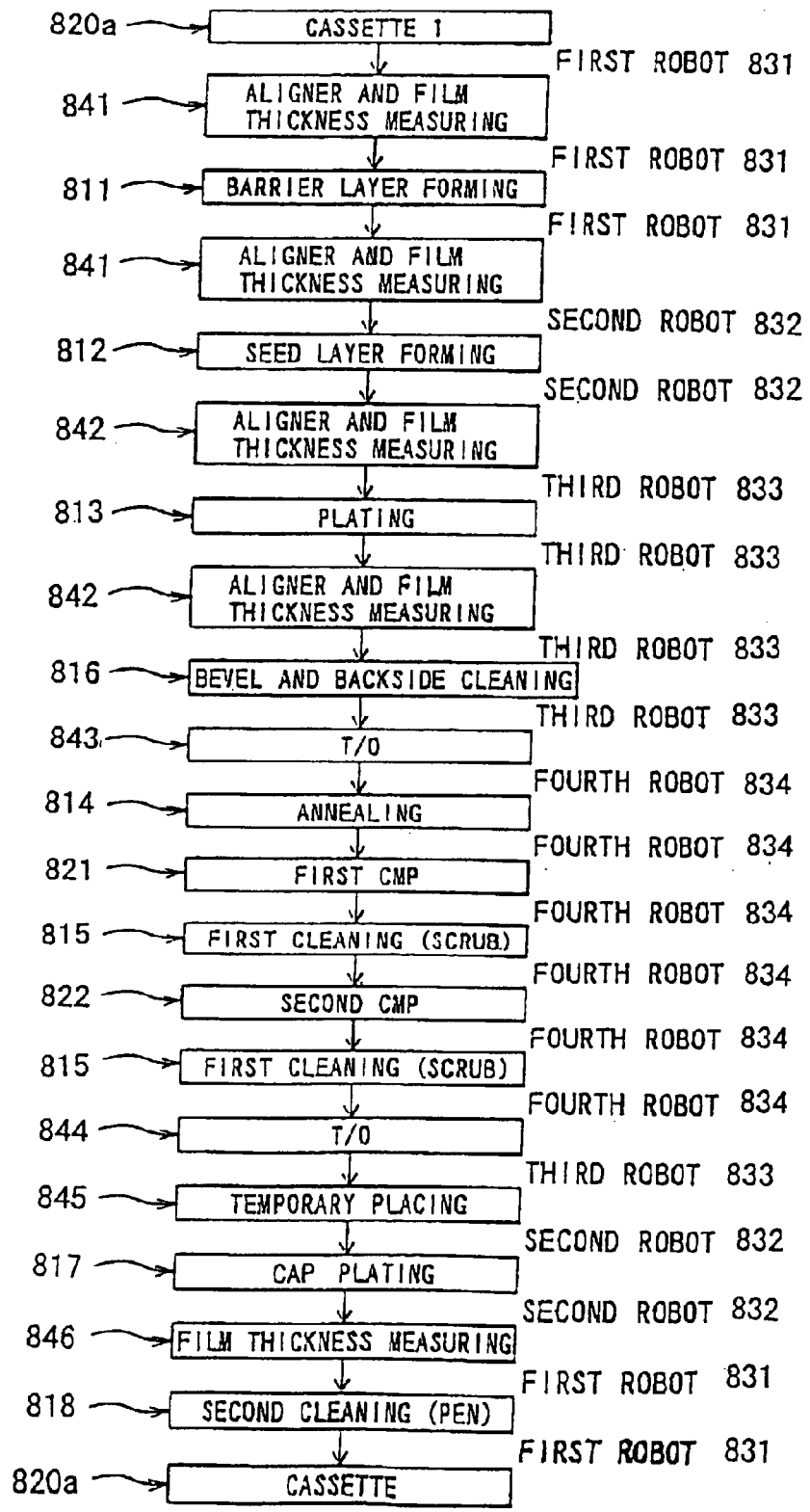
FIG. 18 is a view showing a flow of the respective steps in the semiconductor substrate processing apparatus illustrated in FIG. 17.

FIG. 18 is a flow chart showing the flow of the respective steps in the present substrate processing apparatus. The respective steps in the apparatus will be described according to this flow chart. First, a semiconductor substrate taken out by the first robot 831 from a cassette 820a placed on the load and unload unit 820 is placed in the first aligner and film thickness measuring unit 841, in such a state that its surface, to be plated, faces upward. In order to set a reference point for a position at which film thickness measurement is made, notch alignment for film thickness measurement is performed, and then film thickness data on the semiconductor substrate before formation of a Cu film are obtained.

Then, the semiconductor substrate is transported to the barrier layer forming unit 811 by the first robot 831. The barrier layer forming unit 811 is such an apparatus for forming a barrier layer on the semiconductor substrate by electroless Ru plating, and the barrier layer forming unit 811 forms an Ru film as a film for preventing Cu from diffusing into an interlayer insulator film (e.g. SiO2) of a semiconductor device. The semiconductor substrate discharged after cleaning and drying steps is transported by the first robot 831 to the first aligner and film thickness measuring unit 841, where the film thickness of the semiconductor substrate, i.e., the film thickness of the barrier layer is measured.

After film thickness measurement, the semiconductor substrate is carried into the seed layer forming unit 812 by the second robot 832, and a seed layer is formed on the barrier layer by electroless Cu plating. The semiconductor substrate discharged after cleaning and drying steps is transported by the second robot 832 to the second aligner and film thickness measuring instrument 842 for determination of a notch position, before the semiconductor substrate is transported to the plated film forming unit 813, which is an impregnation plating unit, and then notch alignment for Cu plating is performed by the film thickness measuring instrument 842. If necessary, the film thickness of the semiconductor substrate before formation of a Cu film may be measured again in the film thickness measuring instrument 842.

The semiconductor substrate which has completed notch alignment is transported by the third robot 833 to the plated film forming unit 813 where Cu plating is applied to the semiconductor substrate. The semiconductor substrate discharged after cleaning and drying steps is transported by the third robot 833 to the bevel and backside cleaning unit 816 where an unnecessary Cu film (seed layer) at a peripheral portion of the semiconductor substrate is removed. In the bevel and backside cleaning unit 816, the bevel is etched in a preset time, and Cu adhering to the backside of the semiconductor substrate is cleaned with a chemical liquid such as hydrofluoric acid. At this time, before transporting the semiconductor substrate to the bevel and backside cleaning unit 816, film thickness measurement of the semiconductor substrate may be made by the second aligner and film thickness measuring instrument 842 to obtain the thickness value of the Cu film formed by plating. Based on the obtained results, the bevel etching time may be changed arbitrarily to carry out etching. The region etched by bevel etching is a region which corresponds to a peripheral edge portion of the substrate and has no circuit formed therein, or a region which is not utilized finally as a chip although a circuit is formed. A bevel portion is included in this region.

The semiconductor substrate discharged after cleaning and drying steps in the bevel and backside cleaning unit 816 is transported by the third robot 833 to the substrate reversing machine 843. After the semiconductor substrate is turned over by the substrate reversing machine 843 to cause the plated surface to be directed downward, the semiconductor substrate is introduced into the annealing unit 814 by the fourth robot 834 for thereby stabilizing a interconnection portion. Before and/or after annealing treatment, the semiconductor substrate is carried into the second aligner and film thickness measuring unit 842 where the film thickness of a copper film formed on the semiconductor substrate is measured. Then, the semiconductor substrate is carried by the fourth robot 834 into the first polishing apparatus 821 in which the Cu film and the seed layer of the semiconductor substrate are polished.

At this time, desired abrasive grains or the like are used, but fixed abrasive may be used in order to prevent dishing and enhance flatness of the face. After completion of primary polishing, the semiconductor substrate is transported by the fourth robot 834 to the first cleaning unit 815 where it is cleaned. This cleaning is scrub-cleaning in which rolls having substantially the same length as the diameter of the semiconductor substrate are placed on the face and the backside of the semiconductor substrate, and the semiconductor substrate and the rolls are rotated, while pure water or deionized water is flowed, thereby performing cleaning of the semiconductor substrate.

After completion of the primary cleaning, the semiconductor substrate is transported by the fourth robot 834 to the second polishing apparatus 822 where the barrier layer on the semiconductor substrate is polished. At this time, desired abrasive grains or the like are used, but fixed abrasive may be used in order to prevent dishing and enhance flatness of the face. After completion of secondary polishing, the semiconductor substrate is transported by the fourth robot 834 again to the first cleaning unit 815 where scrub-cleaning is performed. After completion of cleaning, the semiconductor substrate is transported by the fourth robot 834 to the second substrate reversing machine 844 where the semiconductor substrate is reversed to cause the plated surface to be directed upward, and then the semiconductor substrate is placed on the substrate temporary placing table 845 by the third robot.

The semiconductor substrate is transported by the second robot 832 from the substrate temporary placing table 845 to the cap plating unit 817 where cap plating is applied onto the Cu surface with the aim of preventing oxidation of Cu due to the atmosphere. The semiconductor substrate to which cap plating has been applied is carried by the second robot 832 from the cover plating unit 817 to the third film thickness measuring instrument 146 where the thickness of the copper film is measured. Thereafter, the semiconductor substrate is carried by the first robot 831 into the second cleaning unit 818 where it is cleaned with pure water or deionized water. The semiconductor substrate after completion of cleaning is returned into the cassette 820a placed on the loading and unloading section 820.

The aligner and film thickness measuring instrument 841 and the aligner and film thickness measuring instrument 842 perform positioning of the notch portion of the substrate and measurement of the film thickness.

Figure 19:
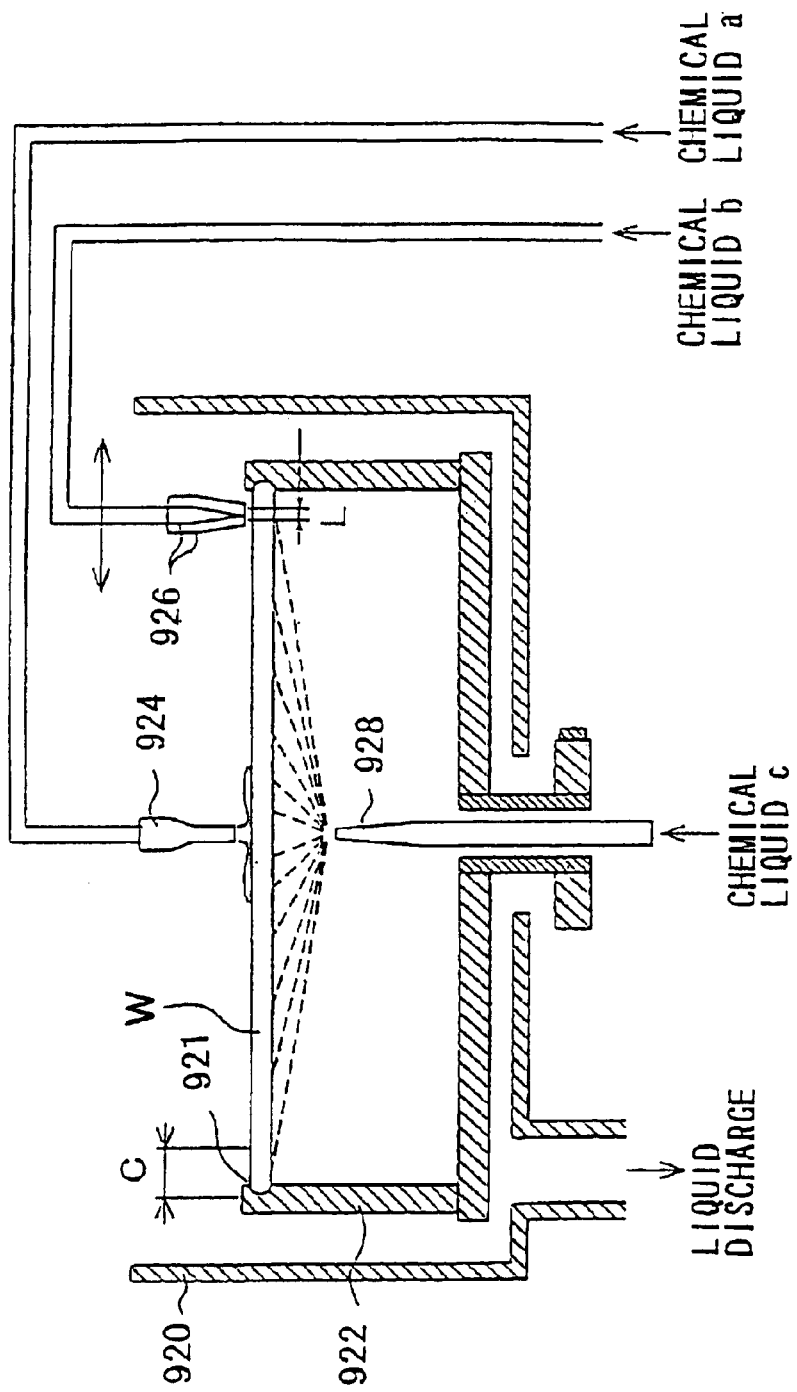
FIG. 19 is a view showing a schematic constitution example of a bevel and backside cleaning unit.

The bevel and backside cleaning unit 816 can perform an edge (bevel) Cu etching and a backside cleaning at the same time, and can suppress growth of a natural oxide film of copper at the circuit formation portion on the surface of the substrate. FIG. 19 shows a schematic view of the bevel and backside cleaning unit 816. As shown in FIG. 19, the bevel and backside cleaning unit 816 has a substrate holding portion 922 positioned inside a bottomed cylindrical waterproof cover 920 and adapted to rotate a substrate W at a high speed, in such a state that the face of the substrate W faces upwardly, while holding the substrate W horizontally by spin chucks 921 at a plurality of locations along a circumferential direction of a peripheral edge portion of the substrate; a center nozzle 924 placed above a nearly central portion of the face of the substrate W held by the substrate holding portion 922; and an edge nozzle 926 placed above the peripheral edge portion of the substrate W. The center nozzle 924 and the edge nozzle 926 are directed downward. A back nozzle 928 is positioned below a nearly central portion of the backside of the substrate W, and directed upward. The edge nozzle 926 is adapted to be movable in a diametrical direction and a height direction of the substrate W.

The width of movement L of the edge nozzle 926 is set such that the edge nozzle 226 can be arbitrarily positioned in a direction toward the center from the outer peripheral end surface of the substrate, and a set value for L is inputted according to the size, usage, or the like of the substrate W. Normally, an edge cut width C is set in the range of 2 mm to 5 mm. In the case where a rotational speed of the substrate is a certain value or higher at which the amount of liquid migration from the backside to the face is not problematic, the copper film within the edge cut width C can be removed.

Next, the method of cleaning with this cleaning apparatus will be described. First, the semiconductor substrate W is horizontally rotated integrally with the substrate holding portion 922, with the substrate being held horizontally by the spin chucks 921 of the substrate holding portion 922. In this state, an acid solution is supplied from the center nozzle 924 to the central portion of the face of the substrate W. The acid solution may be a non-oxidizing acid, and hydrofluoric acid, hydrochloric acid, sulfuric acid, citric acid, oxalic acid, or the like is used. On the other hand, an oxidizing agent solution is supplied continuously or intermittently from the edge nozzle 926 to the peripheral edge portion of the substrate W. As the oxidizing agent solution, one of an aqueous solution of ozone, an aqueous solution of hydrogen peroxide, an aqueous solution of nitric acid, and an aqueous solution of sodium hypochlorite is used, or a combination of these is used.

In this manner, the copper film, or the like formed on the upper surface and end surface in the region of the peripheral edge portion C of the semiconductor substrate W is rapidly oxidized with the oxidizing agent solution, and is simultaneously etched with the acid solution supplied from the center nozzle 924 and spread on the entire face of the substrate, whereby it is dissolved and removed. By mixing the acid solution and the oxidizing agent solution at the peripheral edge portion of the substrate, a steep etching profile can be obtained, in comparison with supplying a mixture of the solutions which is produced in advance. At this time, the copper etching rate is determined by their concentrations. If a natural oxide film of copper is formed in the circuit-formed portion on the face of the substrate, this natural oxide is immediately removed by the acid solution spreading on the entire face of the substrate according to rotation of the substrate, and does not grow any more. After the supply of the acid solution from the center nozzle 924 is stopped, the supply of the oxidizing agent solution from the edge nozzle 926 is stopped. As a result, silicon exposed on the surface is oxidized, and deposition of copper can be suppressed.

On the other hand, an oxidizing agent solution and a silicon oxide film etching agent are supplied simultaneously or alternately from the back nozzle 928 to the central portion of the backside of the substrate. Therefore, copper or the like adhering in a metal form to the backside of the semiconductor substrate W can be oxidized with the oxidizing agent solution, together with silicon of the substrate, and can be etched and removed with the silicon oxide film etching agent. This oxidizing agent solution is preferably the same as the oxidizing agent solution supplied to the face, because the types of chemicals are decreased in number. Hydrofluoric acid can be used as the silicon oxide film etching agent, and if hydrofluoric acid is used as the acid solution on the face of the substrate, the types of chemicals can be decreased in number. Thus, if the supply of the oxidizing agent is stopped first, a hydrophobic surface is obtained. If the etching agent solution is stopped first, a water-saturated surface (a hydrophilic surface) is obtained, and thus the backside surface can be adjusted to a condition which will satisfy the requirements of a subsequent process.

In this manner, the acid solution, i.e., etching solution is supplied to the substrate to remove metal ions remaining on the surface of the substrate W. Then, pure water is supplied to replace the etching solution with pure water and remove the etching solution, and then the substrate is dried by spin-drying. In this way, removal of the copper film in the edge cut width C at the peripheral edge portion on the face of the semiconductor substrate, and removal of copper contaminants on the backside are performed simultaneously to thus allow this treatment to be completed, for example, within 80 seconds. The etching cut width of the edge can be set arbitrarily (to 2 mm to 5 mm), but the time required for etching does not depend on the cut width.

Annealing treatment performed before the CMP process and after plating has a favorable effect on the subsequent CMP treatment and on the electrical characteristics of interconnection. Observation of the surface of broad interconnection (unit of several micrometers) after the CMP treatment without annealing showed many defects such as microvoids, which resulted in an increase in the electrical resistance of the entire interconnection. Execution of annealing ameliorated the increase in the electrical resistance. In the absence of annealing, thin interconnections showed no voids. Thus, the degree of grain growth is presumed to be involved in these phenomena. That is, the following theory can be developed: Grain growth is difficult to occur in thin interconnections. In broad interconnections, on the other hand, grain growth proceeds in accordance with annealing treatment. During the process of grain growth, ultrafine pores in the plated film, which are too small to be seen by the SEM (scanning electron microscope), gather and move upward, thus forming microvoid-like depressions in the upper part of the interconnection. The annealing conditions in the annealing unit 814 are such that hydrogen (2% or less) is added in a gas atmosphere, the temperature is in the range of 300° C. to 400° C., and the time is in the range of 1 to 5 minutes. Under these conditions, the above effects were obtained.

Figure 22:
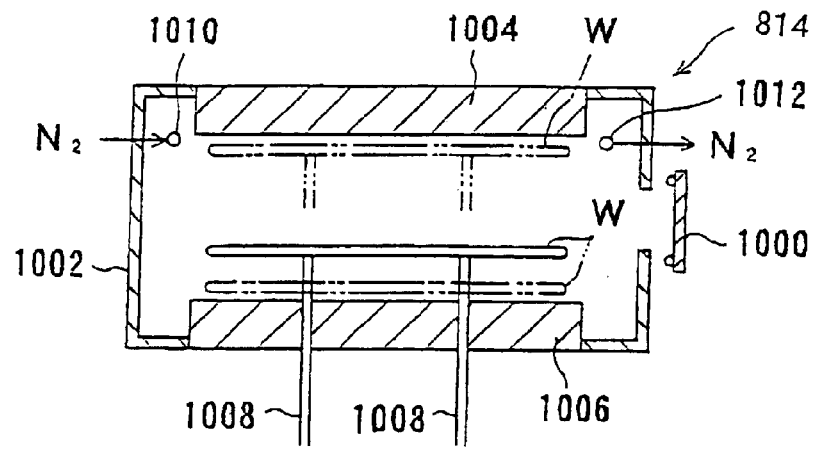
FIG. 22 is a vertical sectional view of an example of an annealing unit.
Figure 23:
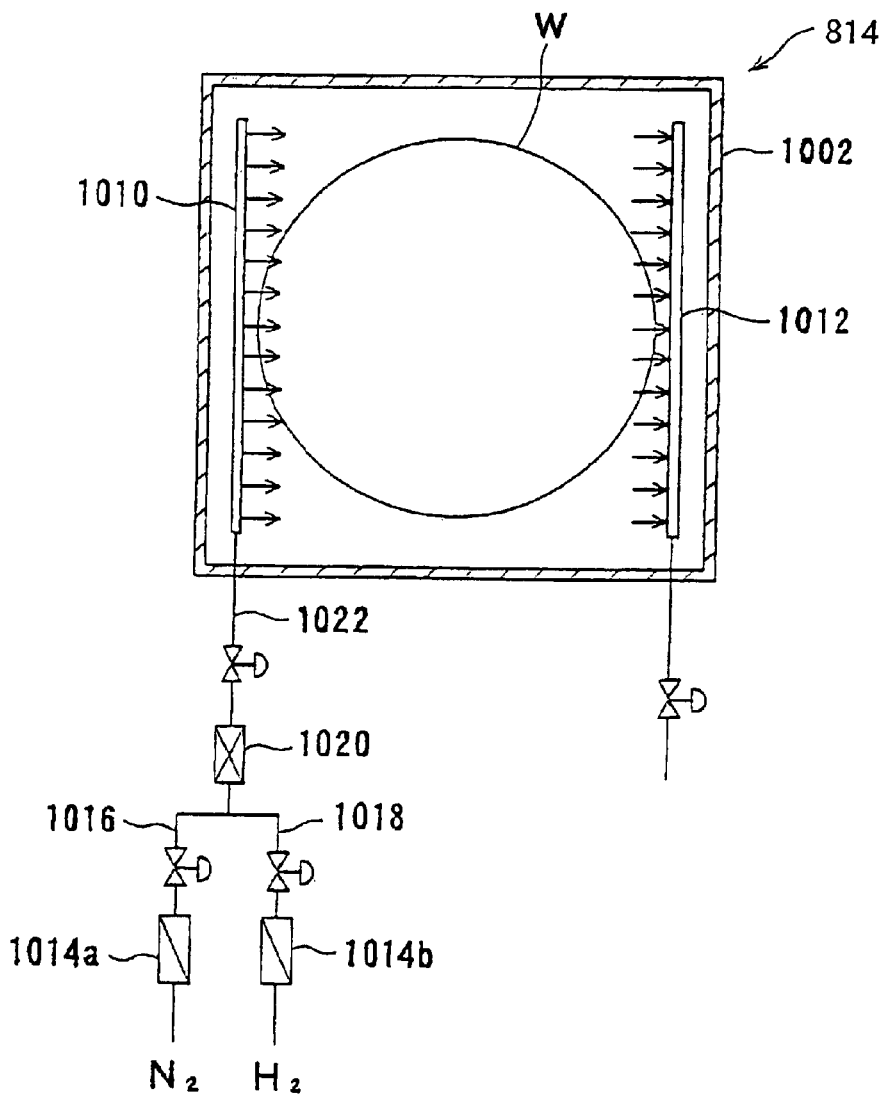
FIG. 23 is a transverse sectional view of the annealing unit.

FIGS. 22 and 23 show the annealing unit 814. The annealing unit 814 comprises a chamber 1002 having a gate 1000 for taking in and taking out the semiconductor substrate W, a hot plate 1004 disposed at an upper position in the chamber 1002 for heating the semiconductor substrate W to e.g. 400° C., and a cool plate 1006 disposed at a lower position in the chamber 1002 for cooling the semiconductor substrate W by, for example, flowing a cooling water inside the plate. The annealing unit 1002 also has a plurality of vertically movable elevating pins 1008 penetrating the cool plate 1006 and extending upward and downward therethrough for placing and holding the semiconductor substrate W on them. The annealing unit further includes a gas introduction pipe 1010 for introducing an antioxidant gas between the semiconductor substrate W and the hot plate 1004 during annealing, and a gas discharge pipe 1012 for discharging the gas which has been introduced from the gas introduction pipe 1010 and flowed between the semiconductor substrate W and the hot plate 1004. The pipes 1010 and 1012 are disposed on the opposite sides of the hot plate 1004.

The gas introduction pipe 1010 is connected to a mixed gas introduction line 1022 which in turn is connected to a mixer 1020 where a $N_2$ gas introduced through a $N_2$ gas introduction line 1016 containing a filter 1014a, and a $H_2$ gas introduced through a $H_2$ gas introduction line 1018 containing a filter 1014b, are mixed to form a mixed gas which flows through the line 1022 into the gas introduction pipe 1010.

In operation, the semiconductor substrate W, which has been carried in the chamber 1002 through the gate 1000, is held on the elevating pins 1008 and the elevating pins 1008 are raised up to a position at which the distance between the semiconductor substrate W held on the lifting pins 1008 and the hot plate 1004 becomes e.g. 0.1–1.0 mm. In this state, the semiconductor substrate W is then heated to e.g. 400° C. through the hot plate 1004 and, at the same time, the antioxidant gas is introduced from the gas introduction pipe 1010 and the gas is allowed to flow between the semiconductor substrate W and the hot plate 1004 while the gas is discharged from the gas discharge pipe 1012, thereby annealing the semiconductor substrate W while preventing its oxidation. The annealing treatment may be completed in about several tens of seconds to 60 seconds. The heating temperature of the substrate may be selected in the range of 100–600° C.

After the completion of the annealing, the elevating pins 1008 are lowered down to a position at which the distance between the semiconductor substrate W held on the elevating pins 1008 and the cool plate 1006 becomes e.g. 0–0.5 mm. In this state, by introducing a cooling water into the cool plate 1006, the semiconductor substrate W is cooled by the cool plate to a temperature of 100° C. or lower in e.g. 10–60 seconds. The cooled semiconductor substrate is sent to the next step.

A mixed gas including $N_2$ gas and a percentage of $H_2$ gas is used as the above antioxidant gas. However, $N_2$ gas may be used singly.

Figure 20:
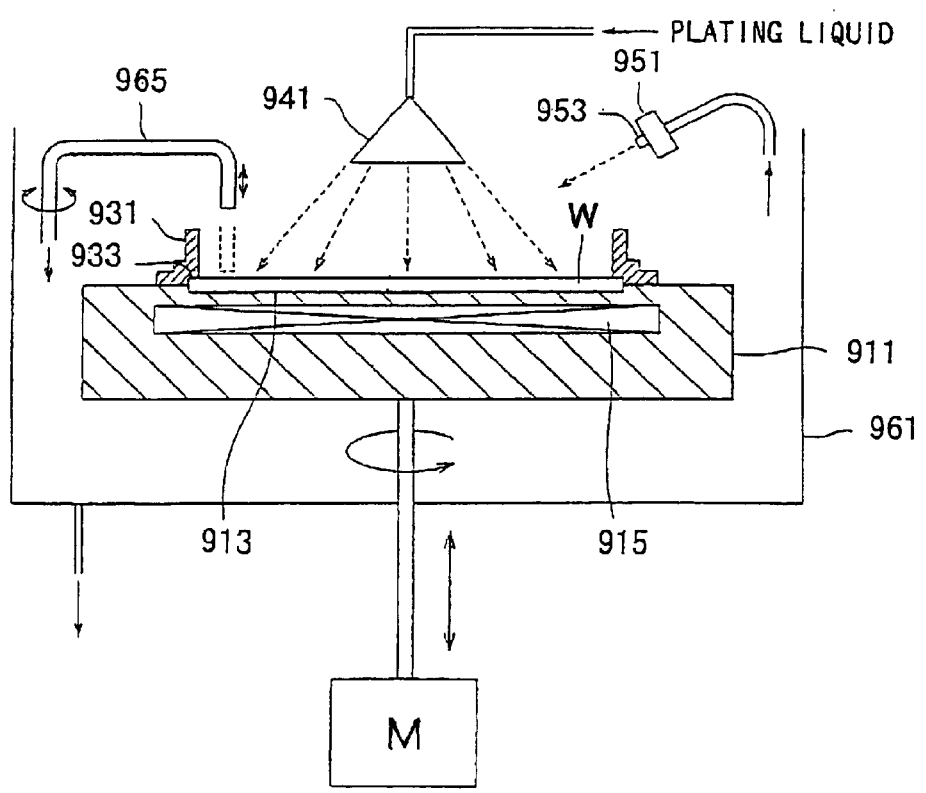
FIG. 20 is a view showing a schematic constitution of an example of an electroless plating apparatus.

FIG. 20 is a schematic constitution drawing of the electroless plating apparatus. As shown in FIG. 20, this electroless plating apparatus comprises holding means 911 for holding a semiconductor substrate W to be plated on its upper surface, a dam member 931 for contacting a peripheral edge portion of a surface to be plated (upper surface) of the semiconductor substrate W held by the holding means 911 to seal the peripheral edge portion, and a shower head 941 for supplying a plating liquid to the surface, to be plated, of the semiconductor substrate W having the peripheral edge portion sealed with the dam member 931. The electroless plating apparatus further comprises cleaning liquid supply means 951 disposed near an upper outer periphery of the holding means 911 for supplying a cleaning liquid to the surface, to be plated, of the semiconductor substrate W, a recovery vessel 961 for recovering a cleaning liquid or the like (plating waste liquid) discharged, a plating liquid recovery nozzle 965 for sucking in and recovering the plating liquid held on the semiconductor substrate W, and a motor M for rotationally driving the holding means 911. The respective members will be described below.

The holding means 911 has a substrate placing portion 913 on its upper surface for placing and holding the semiconductor substrate W. The substrate placing portion 913 is adapted to place and fix the semiconductor substrate W. Specifically, the substrate placing portion 913 has a vacuum attracting mechanism (not shown) for attracting the semiconductor substrate W to a backside thereof by vacuum suction. A backside heater 915, which is planar and heats the surface, to be plated, of the semiconductor substrate W from underside to keep it warm, is installed on the backside of the substrate placing portion 913. The backside heater 915 is composed of, for example, a rubber heater. This holding means 911 is adapted to be rotated by the motor M and is movable vertically by raising and lowering means (not shown).

The dam member 931 is tubular, has a seal portion 933 provided in a lower portion thereof for sealing the outer peripheral edge of the semiconductor substrate W, and is installed so as not to move vertically from the illustrated position.

The shower head 941 is of a structure having many nozzles provided at the front end for scattering the supplied plating liquid in a shower form and supplying it substantially uniformly to the surface, to be plated, of the semiconductor substrate W. The cleaning liquid supply means 951 has a structure for ejecting a cleaning liquid from a nozzle 953.

The plating liquid recovery nozzle 965 is adapted to be movable upward and downward and swingable, and the front end of the plating liquid recovery nozzle 965 is adapted to be lowered inwardly of the dam member 931 located on the upper surface peripheral edge portion of the semiconductor substrate W and to suck in the plating liquid on the semiconductor substrate W.

Next, the operation of the electroless plating apparatus will be described. First, the holding means 911 is lowered from the illustrated state to provide a gap of a predetermined dimension between the holding means 911 and the dam member 931, and the semiconductor substrate W is placed on and fixed to the substrate placing portion 913. An 8 inch wafer, for example, is used as the semiconductor substrate W.

Then, the holding means 911 is raised to bring its upper surface into contact with the lower surface of the dam member 931 as illustrated, and the outer periphery of the semiconductor substrate W is sealed with the seal portion 933 of the dam member 931. At this time, the surface of the semiconductor substrate W is in an open state.

Then, the semiconductor substrate W itself is directly heated by the backside heater 915 to render the temperature of the semiconductor substrate W, for example, 70° C. (maintained until termination of plating). Then, the plating liquid heated, for example, to 50° C. is ejected from the shower head 941 to pour the plating liquid over substantially the entire surface of the semiconductor substrate W. Since the surface of the semiconductor substrate W is surrounded by the dam member 931, the poured plating liquid is all held on the surface of the semiconductor substrate W. The amount of the supplied plating liquid may be a small amount which will become a 1 mm thickness (about 30 ml) on the surface of the semiconductor substrate W. The depth of the plating liquid held on the surface to be plated may be 10 mm or less, and may be even 1 mm as in this embodiment. If a small amount of the supplied plating liquid is sufficient, the heating apparatus for heating the plating liquid may be of a small size. In this example, the temperature of the semiconductor substrate W is raised to 70° C., and the temperature of the plating liquid is raised to 50° C. by heating. Thus, the surface, to be plated, of the semiconductor substrate W becomes, for example, 60° C., and hence a temperature optimal for a plating reaction in this example can be achieved.

The semiconductor substrate W is instantaneously rotated by the motor M to perform uniform liquid wetting of the surface to be plated, and then plating of the surface to be plated is performed in such a state that the semiconductor substrate W is in a stationary state. Specifically, the semiconductor substrate W is rotated at 100 rpm or less for only 1 second to uniformly wet the surface, to be plated, of the semiconductor substrate W with the plating liquid. Then, the semiconductor substrate W is kept stationary, and electroless plating is performed for 1 minute. The instantaneous rotating time is 10 seconds or less at the longest.

After completion of the plating treatment, the front end of the plating liquid recovery nozzle 965 is lowered to an area near the inside of the dam member 931 on the peripheral edge portion of the semiconductor substrate W to suck in the plating liquid. At this time, if the semiconductor substrate W is rotated at a rotational speed of, for example, 100 rpm or less, the plating liquid remaining on the semiconductor substrate W can be gathered in the portion of the dam member 931 on the peripheral edge portion of the semiconductor substrate W under centrifugal force, so that recovery of the plating liquid can be performed with a good efficiency and a high recovery rate. The holding means 911 is lowered to separate the semiconductor substrate W from the dam member 931. The semiconductor substrate W is started to be rotated, and the cleaning liquid (ultrapure water) is jetted at the plated surface of the semiconductor substrate W from the nozzle 953 of the cleaning liquid supply means 951 to cool the plated surface, and simultaneously perform dilution and cleaning, thereby stopping the electroless plating reaction. At this time, the cleaning liquid jetted from the nozzle 953 may be supplied to the dam member 931 to perform cleaning of the dam member 931 at the same time. The plating waste liquid at this time is recovered into the recovery vessel 961 and discarded.

Then, the semiconductor substrate W is rotated at a high speed by the motor M for spin-drying, and then the semiconductor substrate W is removed from the holding means 911.

Figure 21:
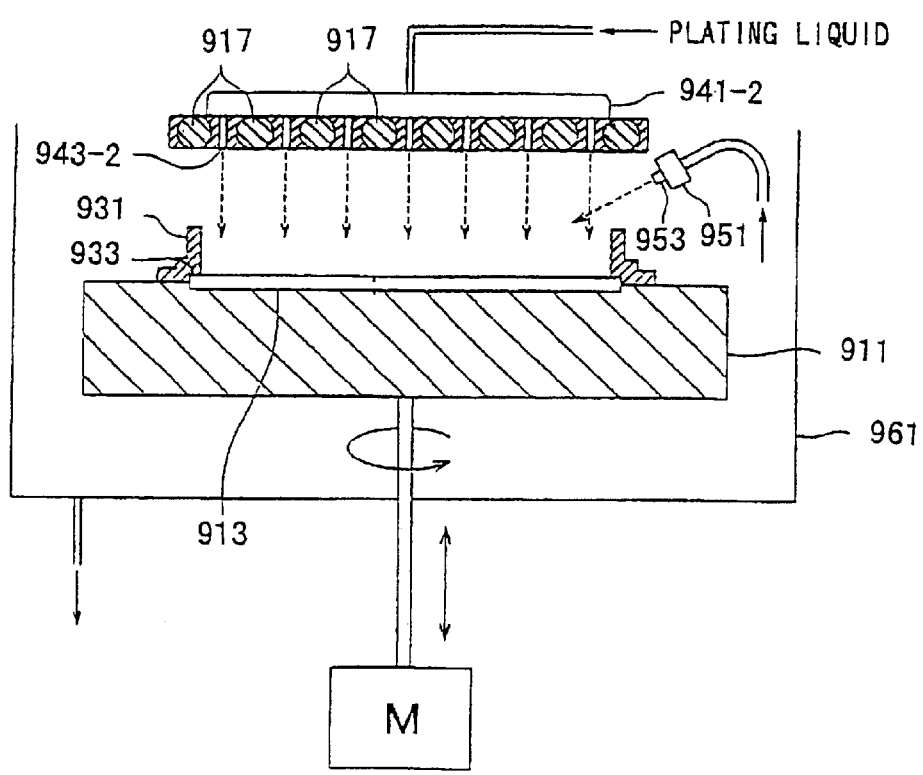
FIG. 21 is a view showing a schematic constitution of another example of an electroless plating apparatus.

FIG. 21 is a schematic constitution drawing of another electroless plating apparatus. The electroless plating apparatus of FIG. 21 is different from the electroless plating apparatus of FIG. 20 in that instead of providing the backside heater 915 in the holding means 911, lamp heaters 917 are disposed above the holding means 911, and the lamp heaters 917 and a shower head 941-2 are integrated. For example, a plurality of ring-shaped lamp heaters 917 having different radii are provided concentrically, and many nozzles 943-2 of the shower head 941-2 are open in a ring form from the gaps between the lamp heaters 917. The lamp heaters 917 may be composed of a single spiral lamp heater, or may be composed of other lamp heaters of various structures and arrangements.

Even with this constitution, the plating liquid can be supplied from each nozzle 943-2 to the surface, to be plated, of the semiconductor substrate W substantially uniformly in a shower form. Further, heating and heat retention of the semiconductor substrate W can be performed by the lamp heaters 917 directly uniformly. The lamp heaters 917 heat not only the semiconductor substrate W and the plating liquid, but also ambient air, thus exhibiting a heat retention effect on the semiconductor substrate W.

Direct heating of the semiconductor substrate W by the lamp heaters 917 requires the lamp heaters 917 with a relatively large electric power consumption. In place of such lamp heaters 917, lamp heaters 917 with a relatively small electric power consumption and the backside heater 915 shown in FIG. 19 may be used in combination to heat the semiconductor substrate W mainly with the backside heater 915 and to perform heat retention of the plating liquid and ambient air mainly by the lamp heaters 917. In the same manner as in the aforementioned embodiment, means for directly or indirectly cooling the semiconductor substrate W may be provided to perform temperature control.

The cap plating described above is preferably performed by an electroless plating process, but may be performed by an electroplating process.

According to the present invention, as described above, the additives in the plating liquid are separated and analyzed (quantified) directly with the liquid chromatography device, and those additives which are insufficient or expected to be insufficient are added to the plating liquid for keeping variations in the amounts of additives in the plating liquid within a certain range. Since the additives in the plating liquid are thus managed, the plating process can be used in a wider range of ultrafine substrate processing applications, and the plating liquid can be used efficiently. Accordingly, the running cost and the environmental load can simultaneously be reduced. Particularly, since the amount of sample liquid required for analysis can significantly be reduced, the running cost and the environmental load can further be reduced.

Although certain preferred embodiments of the present invention have been shown and described in detail, it should be understood that various changes and modifications may be made therein without departing from the scope of the appended claims.

What is claimed is:

1. A method of managing a plating liquid composition, comprising:

sampling a plating liquid in a plating bath;

separating and quantifying an additive in the sampled plating liquid using liquid chromatography by:

introducing the sampled plating liquid and pure water into a separating column to remove ionic components from the plating liquid before the additive is quantified so as to produce ionic component-free sampled plating liquid:

introducing the ionic component-free sampled plating liquid and a hardly soluble liquid into the separating column to elute the additive in the ionic component-free sampled plating liquid; and detecting the intensity of light scattered by an unevaporated solute including the eluted additive remaining after the ionic component-free sampled plating liquid has been evaporated through spraying;

comparing the quantified value of the additive with a given predetermined concentration of the additive; and adding a solution including the additive to the plating liquid based on the compared result.

2. A method of managing a plating liquid composition according to claim 1, further comprising:

separating and quantifying each of a plurality of additives in the sampled plating liquid using liquid chromatography by detecting the intensity of light scattered by an unevaporated solute of each additive remaining after the sampled plating liquid has been evaporated through spraying;

comparing the quantified value of each of the additives with a given predetermined concentration of each of the additives; and adding solutions including the additives to the plating liquid based on the compared result for each of the additives.

3. A method of managing a plating liquid composition according to claim 1, wherein said separating and quantifying an additive further includes detecting the eluted additive using at least one of ultraviolet absorption and differential refraction.

4. A method of managing a plating liquid composition according to claim 3, wherein said separating and quantifying an additive further includes detecting the eluted additive using both said ultraviolet absorption and said differential refraction.

* * * * *